(12) United States Patent
Shin et al.

(10) Patent No.: US 8,080,387 B2
(45) Date of Patent: Dec. 20, 2011

(54) METHOD FOR PREPARING SOLUBLE AND ACTIVE RECOMBINANT PROTEINS USINS PDI AS A FUSION PARTNER

(75) Inventors: Hang-Cheol Shin, Seoul (KR); Yean-Hee Park, Seoul (KR); Hyang-Do Song, Gyeongsangnam-do (KR); Eung-Yoon Kim, Seoul (KR); Ha-A-Rin Chon, Jeollanam-do (KR); Hye-Ran Hyun, Seoul (KR)

(73) Assignee: Vexxon, Inc., Seoul (KR)

( * ) Notice: Subject to any disclaimer, the term of this patent is extended or adjusted under 35 U.S.C. 154(b) by 513 days.

(21) Appl. No.: 12/091,291

(22) PCT Filed: Oct. 24, 2005

(86) PCT No.: PCT/KR2005/003543
§ 371 (c)(1),
(2), (4) Date: Oct. 16, 2008

(87) PCT Pub. No.: WO2007/049829
PCT Pub. Date: May 3, 2007

(65) Prior Publication Data
US 2009/0305351 A1      Dec. 10, 2009

(51) Int. Cl.
*C12N 15/01* (2006.01)
*A61K 38/00* (2006.01)

(52) U.S. Cl. .................. 435/69.1; 435/320.1; 435/70.1; 536/23.1

(58) Field of Classification Search .................. None
See application file for complete search history.

(56) References Cited

U.S. PATENT DOCUMENTS 7,037,684 B2 * 5/2006 Udaka et al. ................. 435/69.4
2004/0018596 A1   1/2004 Udaka et al.

FOREIGN PATENT DOCUMENTS

WO      WO 2007049829 A1 *  5/2007

OTHER PUBLICATIONS

English language abstract for JP 11075879; publication date Mar. 23, 1999; 1 pg; espacenet.com/textdoc?DB=EPODOC&IDX=JP11075879&F=0.
De Sutter, Kristine, Hostens, Katleen, Vandekerckhove. Joël and Fiers, Walter. "Production of enzymatically active rat protein disulfide isomerase in *Escherichia coli*", Gene, vol. 141(2); (1994); pp. 163-170.

Ostermeier, Marc, De Sutter, Kristine and Georgiou, George, "Eukaryotic Protein Dusulfide Isomerase Complements *Escherichia coli dsdA* Mutants and Increases the Yield of a Heterologous Secreted Protein with Disulfied Bonds", The Journal of Biological Chemistry, vol. 271, No. 18, May 3, 1996, pp. 10616-10622.
Niemitalo, Olli, Neubauer, Antje, Liebal, Ulf, Myllyharju, Johanna, Juffer, André and Neubauer, Peter, "Modelling of translation of human protein disulfide isomerase in *Esherichia coli*—A case study of gene optimization", Journal of Biotechnology, vol. 120(1), Oct. 17, 2005, pp. 11-24.
Bessette, Paul H., Aslund. Fredrik, Beckwith, Jon and Georgiou, George, Efficient folding of Proteins with multiple disulfide bonds in the *Escherichia coli* cytoplasm:, vol. 96, No. 24, Nov. 11, 1999, pp. 13703-13708.
Itoh, Nobuyuki, Tanaka, Nobuhiro, Mihashi, Susumu and Yamashina, Ikuo, "Molecular Cloning and Sequence Analysis of cDNA for Batroxobin, a Thrombin-like Snake Venom Enzyme", The Journal of Biological Chemistry, vol. 262, No, 7, Mar. 5, 1987, pp. 3132-3135.
Kapust, Rachel B. and Waugh, David S., "*Escherichia coil* maltose-binding protein is uncommonly effective at promoting the solubility of Polypeptides to which it is fused", Protein Science, vol. 8, (1999) pp. 1668-1674.
Kajino, Tsutomu, Ohto, Chikara, Muramatsu, Masayoshi, Obata, Shusei, Udaka, Shigezo, Yamada, Yukio and Takahashi, Haruo°, "A Protein Disulfide Isomerase Gene Fusion Expression System That Increase the Extracellular Productivity of *Bacillus brevis*" Applied and Environmental Microbiology, Feb. 2000, pp. 638-642.
Puig, Alberto and Gilbert, Hiram F., "Protein Disulfide Isomerase Exhibits Chaperone and Anti-chaperone Activity in the Oxidative Refolding of Lysozyme", The Journal of Biological Chemistry, vol. 269, No. 10, Mar. 11, 1994, pp. 7764-7771.
Rothman, James E., "Polypeptide Chain Binding Proteins: Catalysts of Protein Folding and Related Processes in Cells", Cell, vol. 59, Nov. 17, 1989, pp. 591-601.
International Search Report for International Application No. PCT/KR2005/003543, date of mailing Jul. 11, 2006; 3 pgs.

\* cited by examiner

*Primary Examiner* — Anand Desai
*Assistant Examiner* — Samuel Liu
(74) *Attorney, Agent, or Firm* — Edwards Angell Palmer & Dodge LLP; Kongsik Kim

(57) ABSTRACT

The present invention relates to a method for producing a recombinant protein capable of increasing expression rate of a target protein and also improving solubility and folding of the expressed target protein using a modified protein disulfide isomerase (PDI) as a fusion partner, and an expression vector containing the modified PDI gene as a fusion partner. The method for preparing a recombinant protein using a modified PDI as a fusion partner according to the present invention may solve the problems concerning a low yield and solubility and folding that conventional fusion partners have, and be widely used for protein drug and industrial protein production.

12 Claims, 10 Drawing Sheets self cleavage of EKL

METHOD FOR PREPARING SOLUBLE AND ACTIVE RECOMBINANT PROTEINS USINS PDI AS A FUSION PARTNER

TECHNICAL FIELD

The present invention relates to a method for producing a recombinant protein, which has improved solubility and folding, as well as a high expression rate, employing protein disulfide isomerase (PDI) as a fusion partner, and an expression vector containing a PDI gene as a fusion partner.

More particularly, the present invention relates to a method for preparing a recombinant protein capable of increasing an expression rate of a desired target protein and also improving solubility and folding of the expressed target protein employing a modified PDI as a fusion partner, wherein the modified PDI is obtained by removing a ribosome binding site from a normal PDI by means of a genetic modification and adding a sequence lysine-isoleucine-glutamic acid-glutamic acid-glycine-lysine (KIEEGK (SEQ ID NO: 37), referred to as "M6") to an amino terminus of the normal PDI, the ribosome binding site being present in common in PDI sequences derived from many species, and the target protein is produced by expressing the PDI and the target protein in a form of fusion protein in which the PDI and target protein are bound through a peptide bond, and an expression vector containing a modified PDI gene as a fusion partner.

BACKGROUND ART

Bioindustries, in which physiologically active proteins such as insulins, growth hormones, interferons, enzymes, etc. are produced in microorganisms, have grown rapidly with development of genetic recombination technologies. In recent years, high-speed/high-efficiency production of proteins has taken a very important location in various fields of structural and functional genomics, possession of target proteins for screening new drugs in various post-genome studies, etc. Until now, microorganisms (*Escherichia coli*, yeast), mammalian cells, etc. have been used for protein production, but protein production systems in organisms, which are the most suitable for the high-speed/high-efficiency protein production which is the heart in the studies of the functional genomics, has been known as an *E-coli* system which grows rapidly and is the most studied area in microbiological and physiological fields.

The protein production systems using *E-coli* have an excellent economic efficiency in view of the cost and accommodations, but they have one major problem that a majority of eukaryotic proteins are produced in a form of inclusion bodies, which are precipitates in cells, other than active forms since the proteins are not exactly folded into the active forms when the eukaryotic proteins are produced in cytoplasm of the prokaryotic *E-coli*. In order to obtain the active proteins from the inclusion bodies, the inclusion bodies should be solubilized in a high concentration of guanidine-HCl, and then refolded into an active form using methods such as dilution, etc. It has been known that large amounts of time and expense are required for finding effective refolding conditions since the refolding mechanism has not been found in full and refolding conditions are different in every protein. Highly expensive apparatuses are required for mass-production of a desired protein due to a low refolding yield of the protein, and it is difficult or impossible to refold a majority of high molecular weight proteins, which is an obstacle to industrial applications of the proteins. The inclusion body is formed since intermolecular aggregation of protein-folding intermediates appears during the folding process even if the active proteins are in the most stable form in a thermodynamic aspect [Mitraki, A. & King, J. (1989) Bio/Technology 7: 690-697]. Another reason is why disulfide bonds in the protein should be suitably formed so that the proteins can be biologically active, but the disulfide bonds in the proteins are not suitably formed in *E-coli* cytoplasm due to its reducing condition when the proteins are expressed in the *E-coli* cytoplasm.

As described above, the method, in which the genetically recombinant protein is produced in an active form, will be successfully carried out when the folding and disulfide bonding procedures are satisfied at the same time, and therefore it is difficult to produce a desired protein in the most cases. Also, it has been known that high molecular weight antibody proteins, tissue-type plasminogen activators, factor VIII, etc. are produced in forms of inclusion bodies in an *E-coli* system, and it is very difficult to obtain the proteins in active forms through the refolding process. In order to solve the above problems caused when a recombinant protein is produced in a form of inclusion body, it is important to express the recombinant protein in *E-coli* in a soluble form.

Up to now, there have been methods for expressing a recombinant protein in a soluble form: (i) the first one is a method where a recombinant protein is designed to secrete into *E-coli* periplasm to obtain a soluble form of the protein [Stader, J. A. & Silhavy, T. J. (1970) Methods Enzymol. 165: 166-187], but the method has a low industrial efficiency due to a low expression rate of the protein. (ii) The second one is a method where a soluble form of a recombinant protein is obtained by co-expressing a recombinant protein gene and chaperone genes such as GroEL, Dna K or the like which is involved in the protein folding [Goloubinoff, P. et al. (1989) Nature 337: 44-47], but the method is not general in preventing the formation of inclusion bodies since the method is applicable to specific proteins. (iii) The third one is a method wherein a soluble protein is obtained by selecting a protein, expressed in a soluble form in *E-coli*, as a fusion partner and fusing the desired recombinant protein with a carboxyl terminus of the fusion partner. Until now, the various proteins have been known as the fusion partners, including maltose-binding protein [Kapust, R. B. & Waugh, D. S. (1999) Protein Sci. 8: 1668-1674], NusA [Davis, G. D. et al. (1999) Biotechnol. Bioeng. 65: 382-388], glutathione-S-transferase [Smith, D. B. & Johnson, K. S. (1988) Gene 67: 31-40], thioredoxin [Lavallie, E. R. et al. (1993) Bio/Technology 11: 187-193], Protein-A [Nilsson, B. et al. (1985) Nucleic Acid Res. 13: 1151-1162], an amino terminal domain of transcription initiation factor IF2 [Sorensen, H. P. et al. (2003) Protein Expr. Purif. 32: 252-259], lysil-tRNA synthetase [Choi, Sung-il & Seong, Beak-Lin (1999) Korea Patent No. 10-203919], etc. However, the fusion partners have problems in view of their applications since they are merely expected to improve protein solubility but not to satisfy the protein folding and disulfide bonding at the same time.

Protein disulfide isomerase (PDI), which is an enzyme for catalyzing a thiol:disulfide bond exchange reaction, is found at a high concentration in endoplasmic reticulum in cells. It has been known that, amongst about 20 protein factors known as protein folding regulators in the cells up to the present date, proteins having a catalytic activity, such as PDI, are by no means common [Rothman, J. E. (1989) Cell 59: 591-601]. The PDI facilitates the exact formation of disulfide bonds in proteins by means of the thiol:disulfide bond exchange reaction, and serves as a chaperone when a high concentration of the PDI is present in the cells [Puig, A. & Gilbert, H. F. (1994) J. Biol. Chem. 269: 7764-7771].

Therefore, there have been attempts to produce active proteins by using the PDI. It was reported that PDI from thermophilic fungi is fused with an amino terminus of a target protein to secret a fusion protein from *Bacillus brevis* [Kajino, T. et al. (2000) Appl. Environ. Microbiol. 66: 638-642], or that dsbC, which is a kind of the PDI, is co-expressed with a target protein in an oxidizing cytoplasm of mutant *E-coli* [Bessette, P. H. et al. (1999) Proc. Natl. Acad. Sci. USA, 96: 13703-13708], etc. However, it was revealed that the target protein is produced in a very low yield since it is degraded by proteases secreted by the *Bacillus* strain when the target protein is secreted from the *Bacillus* strain. And, it was also revealed that the target protein has a very low expression rate when it is co-expressed with the dsbC in the cytoplasm.

PDI has a problem that active PDI is expressed at a low level since inactive PDI fragments are produced at the same time due to the presence of ribosome binding sites in the PDI protein. The inventors have found the fact that intact PDI protein other than split PDI protein is stably produced in a soluble form in the cytoplasm if the ribosome binding sites in the PDI protein are removed by means of a genetic modification, and they have designed a novel form of a fusion protein system that may satisfy all effects, such as high expression rate, improved solubility, protein folding, disulfide bonding, etc., by using a genetically engineered PDI as a fusion partner, the genetically engineered PDI being obtained by adding an M6 sequence (KIEEGK (SEQ ID NO: 37)) to an amino terminus of the PDI protein. All recombinant proteins, obtained using a fusion protein system with the genetically engineered PDI protein, were stably produced at a high expression rate and with a high solubility, and exhibited the same or more activity than a wild type PDI protein when the recombinant proteins were degraded through enzymatic cleavage.

DISCLOSURE OF INVENTION

Accordingly, the present invention is designed to solve the problems of the prior art, and therefore it is an object of the present invention to provide a novel method capable of stably producing the proteins at a high expression rate, as well as overcoming problems concerning a low solubility of expressed proteins and a low production of active proteins which were the most problematic when the PDI proteins are produced in *E-col* by satisfying a high expression rate of a target protein, improved production of soluble protein, and protein folding into an active form using PDI as a fusion partner.

In order to accomplish the above object, the present invention provides a method for stably preparing a target protein in a soluble and active form in an *E-coli* strain and simultaneously producing the target protein at a high expression rate using the PDI.

More particularly, the present invention provides a method for producing a fusion protein using a modified PDI protein and a polypeptide as a fusion partner and easily purifying the fusion protein through enzymatic cleavage, wherein the modified PDI protein is obtained by removing a ribosome binding site from a rat PDI gene by means of a genetic modification and adding a M6 sequence (KIEEGK (SEQ ID NO: 37)) to an amino terminus of the rat PDI gene, the polypeptide has an enzymatic cleavage site to a carboxyl terminus thereof, and the fusion protein is obtained by connecting the fusion partner with a target protein through the peptide bonds.

DNA sequences of the genetically modified rat PDI gene were designed according to the present invention and listed as follows. An underlined region is a modified gene sequence for the purpose of removing a ribosome binding site, and a darkened region is a M6 sequence added to enhance an expression rate.

```
   1 AAAATCGAAG AAGGTAAAGA CGCTCTGGAG GAGGAGGACA
     ACGTCCTGGT GCTGAAGAAG

61 AGCAACTTCG CAGAGCCGGC GGCGCACAAC TACCTGCTGG
     TGGAGTTCTA TGCCCCATGG

121 TGTGGCCACT GCAAAGCACT GGCCCCAGAG TATGCCAAAG
     CTGCTGCAAA ACTGAAGGCA

181 GAAGGCTCTG AGATCCGACT AGCAAAGGTG GACGCCACAG
     AAGAGTCTGA CCTGGCCCAG

241 CAGTATGGTG TCCGTGGCTA CCCCACAATC AAGTTCTTCA
     AGAATGGAGA CACAGCCTCC

301 CCAAAGGAAT ATACAGCTGG CAGGGAAGCT GACGACATTG
     TGAACTGGCT GAAGAAACGC

361 ACAGGCCCAG CAGCCACAAC CCTGTCTGAC ACTGCAGCTG
     CAGAGTCCTT GGTGGACTCA

421 AGCGAAGTGA CGGTCATCGG CTTCTTCAAG GACGCAGGGT
     CAGACTCCGC CAAGCAGTTC

481 TTGCTGGCAG CAGAGGCTGT TGATGACATA CCTTTTGGAA
     TCACTTCCAA TAGCGATGTG

541 TTTTCCAAGT ACCAGCTGGA CAAGGATGGG GTGGTCCTCT
     TTAAGAAGTT TGATGAAGGC

601 CGCAACAATT TTGAAGGTGA GATCACCAAG GAGAAGCTAT
     TAGACTTCAT CAAGCACAAC

661 CAGCTGCCTT TGGTCATCGA GTTCACTGAA CAGACAGCTC
     CAAAGATTTT CGGAGGTGAA

721 ATCAAGACAC ATATTCTGCT GTTCCTGCCC AAGAGTGTGT
     CTGACTACGA TGGCAAATTG

781 AGCAACTTTA AGAAAGCGGC CGAGGGCTTT AAGGGCAAGA
     TCCTGTTCAT CTTCATCGAT

841 AGTGACCACA CTGACAACCA GCGCATACTT GAGTTCTTTG
     GCCTGAAGAA GGAGGAATGT

901 CCAGCTGTGC GGCTTATTAC CCTTGATGAA GATATGACCA
     AGTACAAACC GGAGTCAGAC

961 GAGCTGACAG CTGAGAAGAT CACACAATTT TGCCACCACT
     TCCTGGAGGG CAAGATCAAG

1021 CCCCACCTGA TGAGCCAGGA ACTGCCTGAA GACTGGGACA
     GCAGCCAGT GAAAGTGCTA

1081 GTTGGGAAAA ACTTTGAGGA GGTTGCTTTT GATGAGAAAA
     AGAACGTGTT TGTTGAATTC
```

-continued

```
1141 TATGCTCCCT GGTGTGGTCA CTGCAAGCAG CTAGCCCCGA
     TTTGGGATAA ACTGGGAGAG
1201 ACATACAAAG ACCATGAGAA TATCGTCATC GCTAAGATGG
     ACTCAACAGC CAATGAGGTG
1261 GAAGCTGTGA AGGTGCACAG CTTTCCCACA CTCAAGTTCT
     TCCCAGCAAG TGCAGACAGA
1321 ACGGTCATTG ATTACAACGG TGAGCGGACA CTAGATGGTT
     TTAAGAAATT CTTGGAGAGC
1381 GGTGGCCAGG ATGGAGCGGG GGACAATGAC GACCTCGACC
     TAGAAGAAGC TTTAGAGCCA
1441 GATATGGAAG AAGACGACGA TCAGAAAGCC GTGAAGGATG
     AACTG
```

In addition to the rat PDI used in the present invention, many PDI gene sequences from human, cattle, fowl, orangutan, chinese hamster, rabbit, mouse, venomous snake, frog, *drosophila, Fasciola hepatica,* cattle parasite, hookworm, *Caenorhabditis elegans, Brugia malayi,* etc. have a ribosome binding site inside the PDI itself.

These sequences have in common a sequence AGGAGGAG ATG (SEQ ID NO: 42) (an underlined G is G or A) and form a ribosome binding site [Lewin, B., Genes VII, Oxford University Press, pp. 147-148]. Accordingly, a genetically modified PDI gene, in which the ribosome binding site is removed through the genetic modification, may be prepared from all the sequences in the same manner as in the rat PDI gene, and its expression may be stably induced at a high expression rate by adding the M6 sequence to an amino terminus of the modified PDI gene.

The present invention is characterized in that stability, expression rate, solubility and folding of a desired target protein is improved, and the target protein is produced in a form of a fusion protein in which an enzymatic cleavage site is inserted between the genetically modified PDI and the target protein, and then easily purified through the enzymatic cleavage. Also, a histidine tag containing 6-10 histidine residues may be added to an amino terminus or a carboxyl terminus of the genetically modified PDI, or a carboxyl terminus of the target protein for the purpose of the easy purification. In this case, the fusion protein may be easily purified using Ni-chelating affinity column chromatography. In another method used for the easy purification, a peptide sequence containing 6-10 aspartic acid and glutamic acid residues, namely DEDDDE (SEQ ID NO: 38), DEDEDE (SEQ ID NO: 39) or DEDEDEDE (SEQ ID NO: 40), may be added to a carboxyl terminus of the modified PDI.

A transformant may be prepared by introducing an expression vector, which produces the fusion protein, into a suitable host cell, for example *E-coli* strains BL21(DE3), HMS174 (DE3), Rossetta(DE3), etc., and cultivated under suitable conditions to stably produce a soluble and active fusion protein containing a target protein at a high expression rate. The cultivated cells are subject to lysozyme digestion, freezing and thawing, sonication, or French press, etc., and then an aqueous solution containing the fusion protein is obtained using centrifugation, filtration, etc. The fusion protein may be easily isolated with conventional purification methods such as affinity chromatography, ion exchange chromatography, gel filtration, etc. The isolated fusion protein may be treated with a suitable amount of enterokinase or TEV protease, etc to obtain a target protein only.

BRIEF DESCRIPTION OF THE DRAWINGS

These and other features, aspects, and advantages of preferred embodiments of the present invention will be more fully described in the following detailed description, taken accompanying drawings. In the drawings.

BEST MODES FOR CARRYING OUT THE INVENTION

Hereinafter, preferred embodiments of the present invention will be described in detail with reference to the accompanying drawings. However, the description proposed herein is just a preferable example for the purpose of illustrations only, not intended to limit the scope of the invention, so it should be understood that other equivalents and modifications could be made thereto without departing from the spirit and scope of the invention.

Embodiment 1

Construction of pSSB-PDI1 Plasmid Vector

A molecular genetic technique used in the present invention is based on a literature [Ausubel, F. M. et al. (Ed.), J. Wiley Sons, Curr. Protocols in Molecular Biology, 1997]. Primers used for a polymerase chain reaction (PCR) were ordered and synthesized at Bioneer Corp., rTaq polymerase was commercially available from TaKaRa, and PCR was carried out according to a standard condition presented by a TaKaRa's manual protocol.

A PDI gene was cloned by carrying out PCR using cDNA of a rat PDI gene as a template. A fusion protein was designed so that a sequence of 6 amino acid residues (M6) existing in an amino-terminal domain of maltose-binding protein was added to an amino terminus of a PDI protein so as to enhance an expression rate of a PDI protein, and a peptide sequence containing 6 aspartic acid and glutamic acid residues and a linker amino acid residue was added to a carboxyl terminus of the PDI protein for the purpose of its easy purification. At this time, oligonucleotides set forth in SEQ ID NOs: 1 and 2 were used as the primers.

Figure 1:
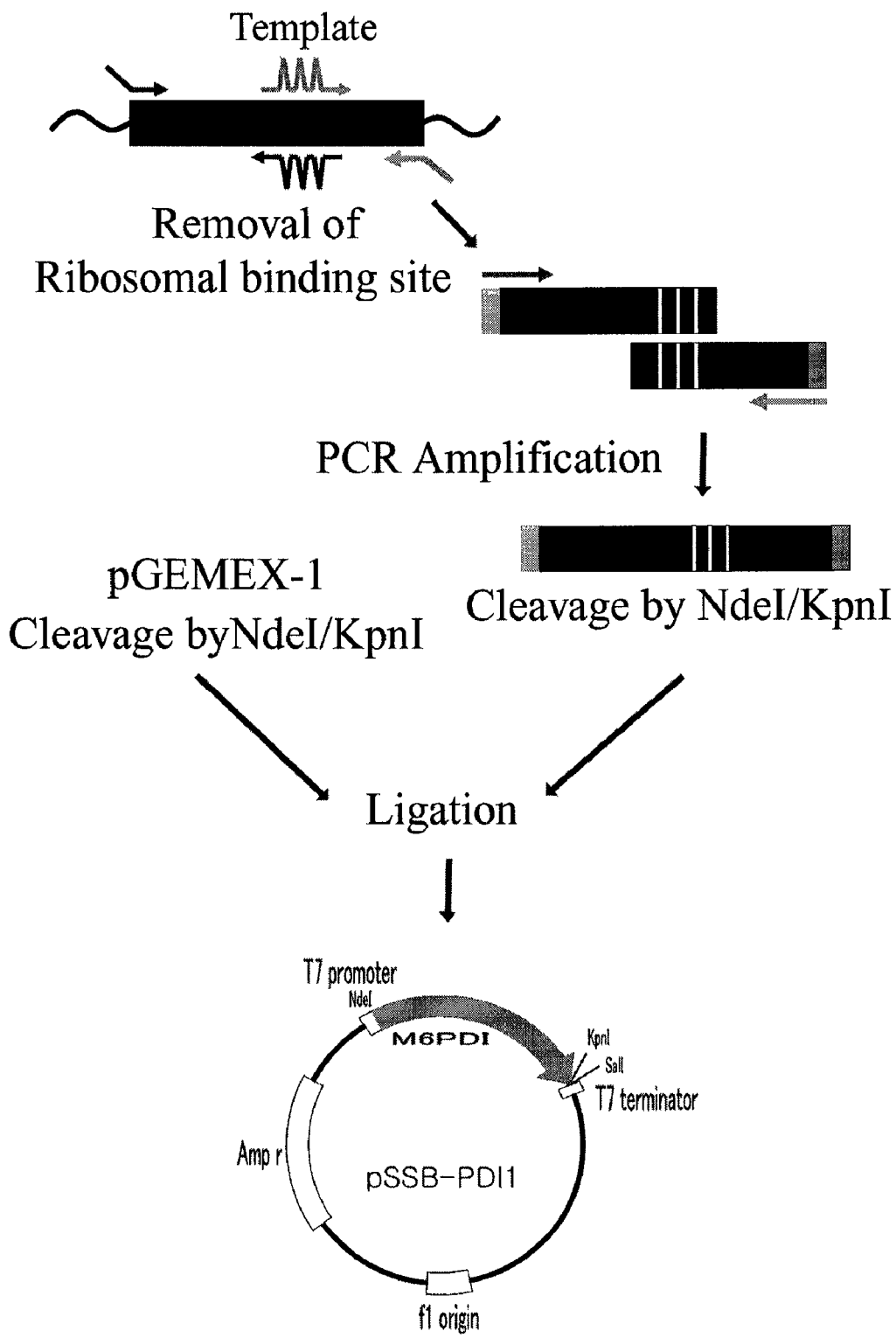
FIG. 1 is a diagram showing an outline of constructing a plasmid vector pSSB-PDI1.

Since the rat PDI gene has a ribosome binding site in the middle thereof, the rat PDI gene was co-expressed with a small-sized PDI fragment, which does not have an activity as the fusion partner. Therefore, in order to remove the ribosome binding site located in the middle of the PDI gene, bases at $911^{th}$, $914^{th}$ and $920^{th}$ nucleotides of the PDI gene were modified using a PCR method using primers set forth in SEQ ID NOs: 3 and 4 (a genetically modified PDI gene: SEQ ID NO: 25 and its protein: SEQ ID NO: 26). At first, the primers set forth in SEQ ID NOs: 1 and 4 were dissolved in a TE (pH 8.0) solution to a density of 10 picomole/µl, respectively, and then PCR was carried out using the primers to amplify a DNA fragment containing the upstream part of the PDI gene. Subsequently, PCR was carried out using equivalent amounts of the primers set forth in SEQ ID NOs: 2 and 3 to amplify a DNA fragment containing the downstream part of the PDI gene. Exact sizes of the DNA fragments were determined in DNA agarose gel (1×TAE, 1% agarose), and DNA bands in the agarose gel were cut and purified with a gel extraction kit (Intron), respectively. The two DNA fragments were mixed at an equivalent amount to obtain a template, and then PCR was carried out using the template and primers set forth in SEQ ID NOs: 1 and 2 to obtain an amplified DNA fragment corresponding to a final M6PDI gene (see FIG. 1).

1 µg of the amplified DNA fragment was dissolved in 50 µl TE (pH 8.0) solution and mixed with 2 units of NdeI (NEB) and 2 units of KpnI (NEB), and then the resultant mixture was reacted at 37° C. for 16 hours to obtain a DNA fragment having an NdeI restriction enzyme recognition site at its 5'-terminus and a KpnI restriction enzyme recognition site at its 3'-terminus. Only the DNA fragment was purified using a DNA purification kit (intron), and a linear pGEMEX-1 plasmid (Promega) was prepared by treating a circular pGEMEX-1 plasmid with restriction enzymes NdeI and KpnI in the same manner as in the above. Subsequently, 20 ng of the DNA fragment and 20 ng of the linear pGEMEX-1 plasmid were mixed in 10 µl TE (pH 8.0) solution, and then the resultant mixture was added 1 unit of T4 DNA ligase (NEB) and reacted at 16° C. for 16 hours to ligate them into one plasmid. The plasmid prepared thus was named pSSB-PDI1 (see FIG. 1).

Embodiment 2

Construction of Expression Plasmid for Production of Tissue-type Plasminogen Activator in Form of Fusion Protein A human tissue-type plasminogen activator (hereinafter, referred to as "tPA") gene was used as a template, and a genetically modified tPA was also used as a template to enhance an expression rate of a target protein considering codon usage.

In order to produce the target protein in a form of fusion protein and remove a fusion partner from the fusion protein, a tPA gene containing a DNA sequence at its 5'-terminus was amplified with a PCR method using primers set forth in SEQ ID NOs: 5 and 6, the DNA sequence encoding an amino acid sequence recognized by TEV enzyme.

Figure 2:
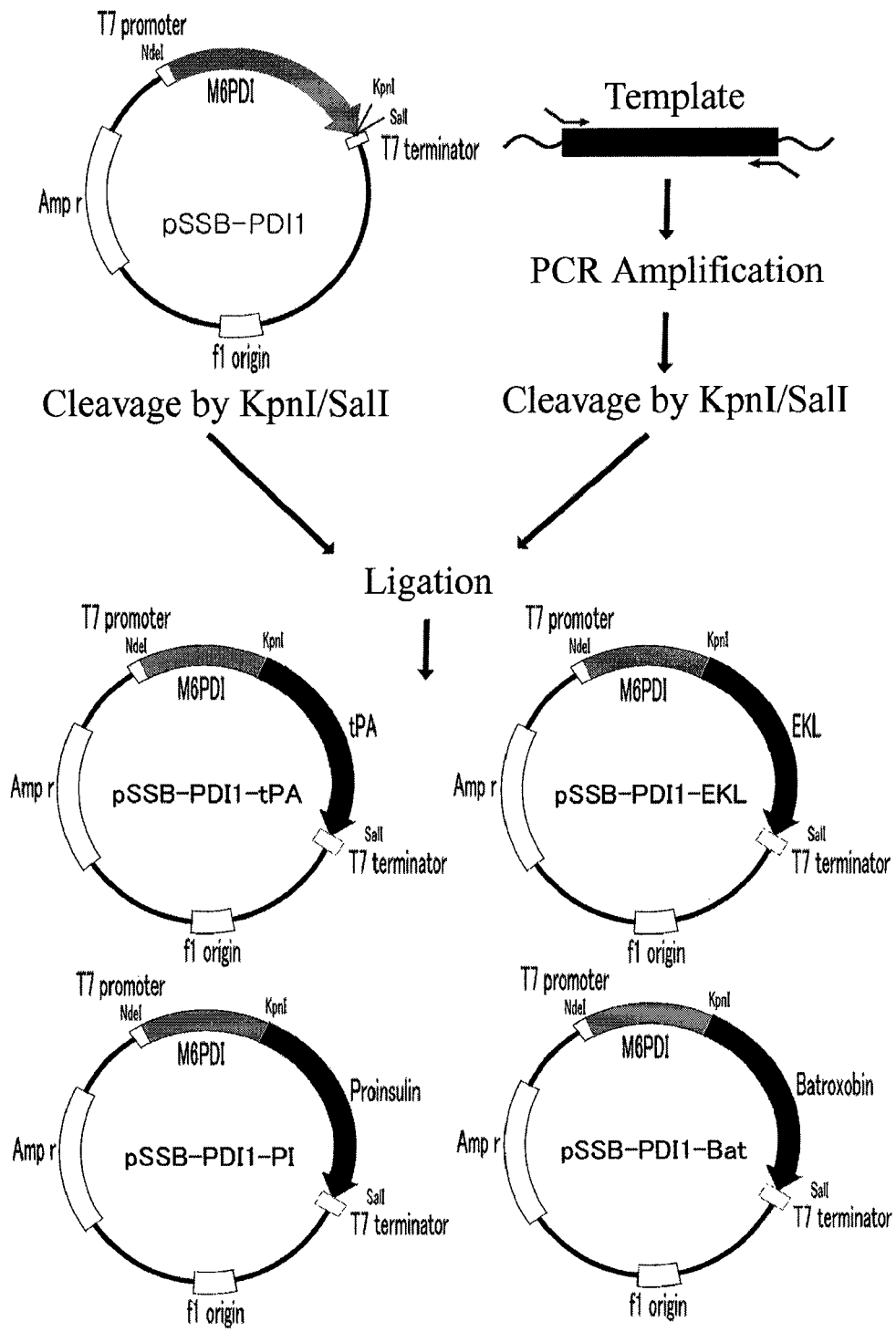
FIG. 2 a diagram showing outlines of constructing plasmid vectors pSSB-PDI1-tPA, pSSB-PDI1-EKL, pSSB-PDI1-PI and pSSB-PDI1-Bat.

1 µg of the amplified DNA fragment was dissolved in 50 µl TE (pH 8.0) solution, and mixed with 2 units of KpnI (NEB), and then the resultant mixture was reacted at 37° C. for 6 hours, and only a DNA fragment was purified with a DNA purification kit (Intron). Also, the purified DNA was dissolved in 50 µl TE (pH 8.0) solution, and mixed with 2 units of SalI (NEB), and then the resultant mixture was reacted at 37° C. for 16 hours to obtain a DNA fragment having a KpnI restriction enzyme recognition site at its 5'-terminus and a SalI restriction enzyme recognition site at its 3'-terminus. The DNA fragment was inserted to the plasmid pSSB-PDI1 which was treated with restriction enzymes KpnI and SalI in the same manner as in the above. The expression plasmid prepared thus was named pSSB-PDI1-tPA (see FIG. 2).

Embodiment 3

Construction of Expression Plasmid for Production of EKL in Form of Fusion Protein EKL is a light chain domain which is an active region of the protease, bovine enterokinase, and only the light chain of the bovine enterokinase was used as a template to clone an EKL gene.

In order to produce the target protein in a form of fusion protein and remove a fusion partner from the fusion protein, an EKL gene was amplified with a PCR method using primers set forth in SEQ ID NOs: 7 and 8, the EKL gene containing a DNA sequence, which encodes an amino acid sequence (DDDDK (SEQ ID NO: 43)) recognized by EKL enzyme, at its amino-terminal domain, and a DNA sequence containing 6 histidine residues at its carboxyl-terminal domain for the purpose of improving its purification.

The amplified DNA fragment was inserted between sites of the plasmid pSSB-PDI1 recognized by restriction enzymes KpnI and SalI in the same manner as in Embodiment 2. The plasmid vector prepared thus was named pSSB-PDI1-EKL (see FIG. 2).

Embodiment 4

Construction of Expression Plasmid for Production of Proinsulin in Form of Fusion Protein Human proinsulin cDNA was used as a template to clone a proinsulin gene.

For the purpose of isolation from a fusion partner and production of insulin, a proinsulin gene was amplified with a PCR method using primers set forth in SEQ ID NOs: 9 and 10, the proinsulin gene containing a DNA sequence encoding 8 histidine residues and 2 arginine residues (RR).

The amplified DNA fragment was inserted between sites of the plasmid pSSB-PDI1 recognized by restriction enzymes KpnI and SalI in the same manner as in Embodiment 2. The plasmid vector prepared thus was named pSSB-PDI1-PI (see FIG. 2).

Embodiment 5

Construction of Expression Plasmid for Production of Batroxobin in Form of Fusion Protein Batroxobin cDNA extracted from a snake *Bothrops atrox moojeni* was used as a template to clone a batroxobin gene [see Itoh, N., Tanaka, N., Mihashi, S. and Yamashina, I. (1987) J. Biol. Chem. 262, 3125-3132].

For the purpose of isolation from a fusion partner, a batroxobin gene was amplified with a PCR method using primers set forth in SEQ ID NOs: 11 and 12, the batroxobin gene containing a DNA sequence encoding a sequence of amino acid residues (ENLYFQ (SEQ ID NO: 44)) recognized by TEV protease.

The amplified DNA fragment was inserted between sites of the plasmid pSSB-PDI1 recognized by restriction enzymes KpnI and SalI in the same manner as in Embodiment 2. The plasmid vector prepared thus was named pSSB-PDI1-Bat (see FIG. 2).

Embodiment 6

Construction of Expression Plasmid for Production of Bone Morphogenetic Protein-2 (BMP-2) in Form of Fusion Protein Human bone morphogenetic protein-2 (hBMP-2) cDNA was used as a template to clone a BMP-2 gene.

For the purpose of isolation from a fusion partner, a BMP-2 gene was amplified with a PCR method using primers set forth in SEQ ID NOs: 13 and 14, the BMP-2 gene containing a DNA sequence encoding a sequence of amino acid residues (ENLYFQ (SEQ ID NO: 44)) recognized by TEV protease.

Figure 3:
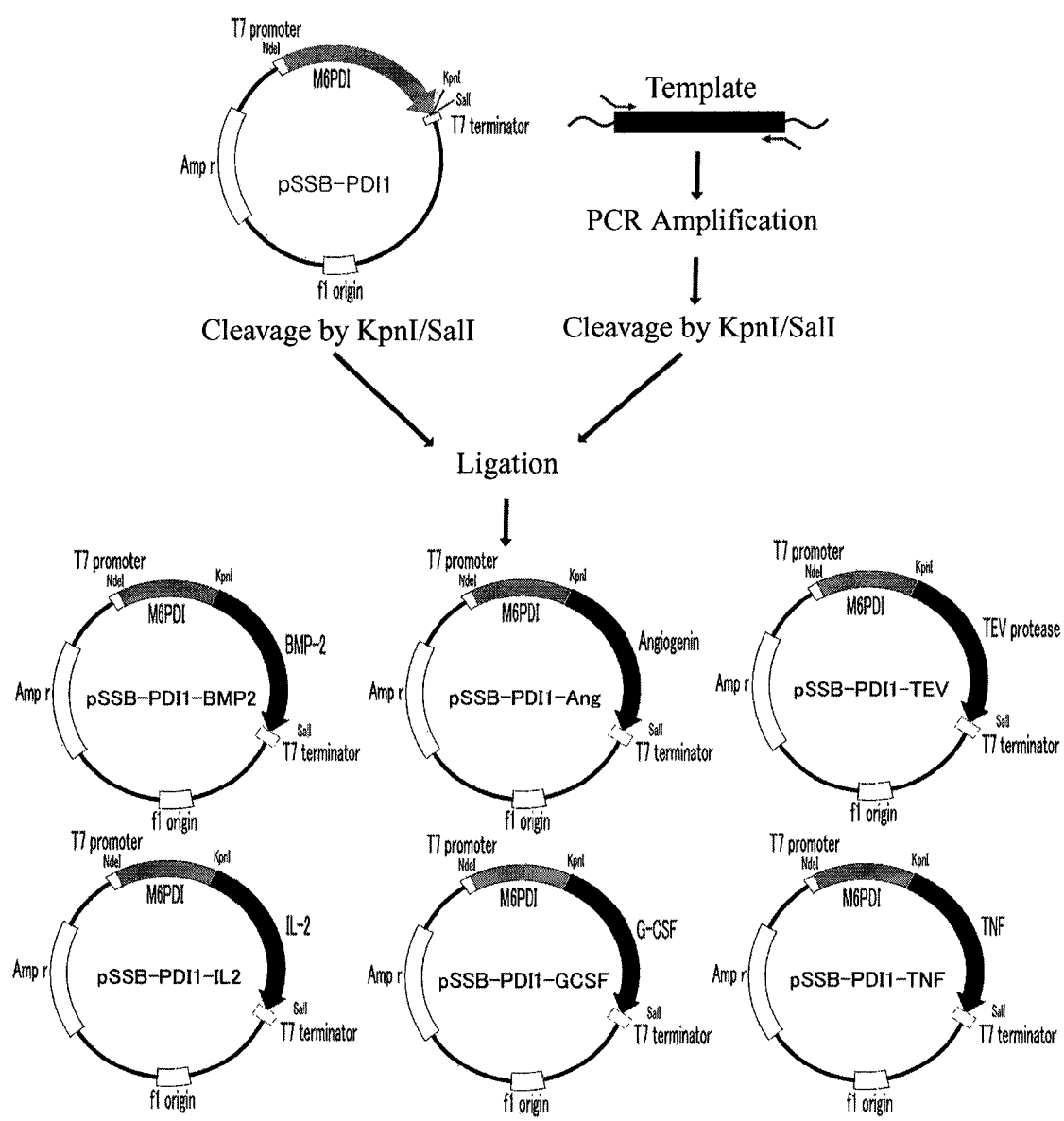
FIG. 3 a diagram showing outlines of constructing plasmid vectors pSSB-PDI1-BMP2, pSSB-PDI1-Ang, pSSB-PDI1-TEV, pSSB-PDI1-IL2, pSSB-PDI1-GCSF and pSSB-PDI1-TNF.

The amplified DNA fragment was inserted between sites of the plasmid pSSB-PDI1 recognized by restriction enzymes KpnI and SalI in the same manner as in Embodiment 2. The plasmid vector prepared thus was named pSSB-PDI1-BMP2 (see FIG. 3).

Embodiment 7

Construction of Expression Plasmid for Production of Angiogenin in Form of Fusion Protein Bovine-derived angiogenin cDNA was used as a template to clone an angiogenin gene.

For the purpose of isolation from a fusion partner, an angiogenin gene was amplified with a PCR method using primers set forth in SEQ ID NOs: 15 and 16, the angiogenin gene containing a DNA sequence encoding a sequence of amino acid residues (ENLYFQ (SEQ ID NO: 44)) recognized by TEV protease.

The amplified DNA fragment was inserted between sites of the plasmid pSSB-PDI1 recognized by restriction enzymes KpnI and SalI in the same manner as in Embodiment 2. The plasmid vector prepared thus was named pSSB-PDI1-Ang (see FIG. 3).

Embodiment 8

Construction of Expression Plasmid for Production of Tobacco Etch Virus (TEV) Protease in Form of Fusion Protein 27 kDa catalytic domain cDNA of NIa (Nuclear Inclusion a), extracted from tobacco etch virus (TEV), was used as a template to clone a TEV protease gene.

For the purpose of isolation from a fusion partner, a TEV protease gene was amplified with a PCR method using primers set forth in SEQ ID NOs: 17 and 18, the TEV protease gene containing a DNA sequence encoding a sequence of amino acid residues (ENLYFQ (SEQ ID NO: 44)) recognized by TEV protease.

The amplified DNA fragment was inserted between sites of the plasmid pSSB-PDI1 recognized by restriction enzymes KpnI and SalI in the same manner as in Embodiment 2. The plasmid vector prepared thus was named pSSB-PDI1-TEV (see FIG. 3).

Embodiment 9

Construction of Expression Plasmid for Production of Interleukin-2 (IL2) in Form of Fusion Protein Human interleukin-2 cDNA was used as a template to clone an IL2 gene.

For the purpose of isolation from a fusion partner, an IL2 gene was amplified with a PCR method using primers set forth in SEQ ID NOs: 19 and 20, the IL2 gene containing a DNA sequence encoding a sequence of amino acid residues (ENLYFQ (SEQ ID NO: 44)) recognized by TEV protease.

The amplified DNA fragment was inserted between sites of the plasmid pSSB-PDI1 recognized by restriction enzymes KpnI and SalI in the same manner as in Embodiment 2. The plasmid vector prepared thus was named pSSB-PDI1-IL2 (see FIG. 3).

Embodiment 10

Construction of Expression Plasmid for Production of Granulocyte Colony Stimulating Factor (GCSF) in Form of Fusion Protein

A PCR method was carried out using human GCSF cDNA as a template to obtain a granulocyte colony stimulating factor (GCSF) gene.

In order to express a target protein and isolate the target protein from a fusion partner, a GCSF gene was amplified with a PCR method using primers set forth in SEQ ID NOs: 21 and 22, the GCSF gene containing a DNA sequence encoding a sequence of amino acid residues (ENLYFQ (SEQ ID NO: 44)) recognized by TEV protease.

The amplified DNA fragment was inserted between sites of the plasmid pSSB-PDI1 recognized by restriction enzymes KpnI and SalI in the same manner as in Embodiment 2. The plasmid vector prepared thus was named pSSB-PDI1-GCSF (see FIG. 3).

Embodiment 11

Construction of Expression Plasmid for Production of Tumor Necrosis Factor-Alpha (TNF-α) in Form of Fusion Protein

Human TNF-α (human Tumor Necrosis Factor-α) cDNA was used as a template to clone a tumor necrosis factor-alpha gene.

In order to express a target protein and isolate the target protein from a fusion partner, a TNF-α gene was amplified with a PCR method using primers set forth in SEQ ID NOs: 23 and 24, the TNF-α gene containing a DNA sequence encoding a sequence of amino acid residues (ENLYFQ (SEQ ID NO: 44)) recognized by TEV protease.

The amplified DNA fragment was inserted between sites of the plasmid pSSB-PDI1 recognized by restriction enzymes KpnI and SalI in the same manner as in Embodiment 2. The plasmid vector prepared thus was named pSSB-PDI1-TNF (see FIG. 3).

Embodiment 12

Preparation of E-coli Transformant

A typical production strain E-coli BL21(DE3), HMS174 (DE3) or Rossetta(DE3) was transformed respectively with the expression plasmid pSSB-PDI1-(tPA, EKL, PI, Bat, BMP2, Ang, TEV, IL2, GCSF, and TNF), prepared in Embodiments 2 to 11, using a method proposed by Hanahan, and ampicillin-resistant colonies were selected, respectively [Hanahan, D. (1985) DNA Cloning vol. 1 (Ed. D. M. Glover) 109-135, IRS press].

The strain E-coli Rosetta(DE3) transformed with the expression vector pSSB-PDI1-tPA was selected and deposited in an international depository authority, the Korean Culture Center of Microorganisms (KCCM, #361-221, Yurim Building, Hongje-1-dong, Seodaemun-gu, Seoul, Republic of Korea) on Jan. 27, 2005 under an accession number of KCCM-10646P according to the Budapest Convention.

Embodiment 13

Cell Culture and Production of Target Protein

Each of the E-coli transformants transformed respectively with the recombinant expression vectors pSSB-PDI1-(tPA, EKL, PI, Bat, TEV, ANG, IL2, BMP-2, GCSF and TNF), prepared in Embodiments 2 to Embodiment 11, was inoculated and cultured in a liquid medium (tryptone 10 g/l, yeast extract 10 g/l, sodium chloride 5 g/l) containing ampicillin (50~100 μg/ml) or ampicillin and chloramphenicol (38~50 μg/ml).

The recombinant E-coli strains were cultured in the liquid medium, and then in a solid medium containing the same components as in the solid medium, and the resultant colonies were cultivated for 12 hours in 1 μl of a liquid medium containing ampicillin (50~100 μg/ml) or ampicillin and chloramphenicol (38~50 μg/ml), and then the colony culture medium was suspended in 15% glycerol solution, which was stored at −70° C. for future use. The recombinant E-coli strains stored at −70° C. were spread on the same solid medium as in the above and cultivated at 37° C. for 16~18 hours to allow colonies to grow on the solid medium, and then the grown colonies were inoculated again in 20 ml liquid medium and cultivated at 37° C. while stirring at a rotary speed of 200 rpm. 16~17 hours after their cultivation, the resultant liquid mediums were inoculated in 400 ml of a liquid medium to a density of 5%, and cultivated at 37° C. while stirring at a rotary speed of 200 rpm, pH 7. When the recombinant E-coli strains were grown to an optimal density of 0.4~0.6 at 600 nm, isopropyl-3-D-thiogalactopyranoside (IPTG, to a final density of 0.5~1 mM) was added to the culture solutions, respectively, and then suspended at 20~25° C. for 4 hours while stirring at a rotary speed of 200 rpm to induce expression of fusion proteins. The resultant culture solutions were centrifuged for 10 minutes at a rotary speed of 6,000 rpm to obtain E-coli pellets, and the pellets were suspended in 20 ml of 50 mM TrisHCl buffer (pH 8.0) and then lysed with a sonication method. The cell lysates lysed with the sonication were centrifuged at 4° C. for 10 minutes at a rotary speed of 13,000 rpm to separate a supernatant fraction and a pellet fraction, and then amounts of fusion proteins in the supernatant fraction and the pellet fraction were determined on SDS-PAGE. As a result, a majority of the fusion proteins were accumulated in a soluble form (FIG. 4 through FIG. 14).

Embodiment 14

Purification and Activity of tPA Protein

Figure 4:
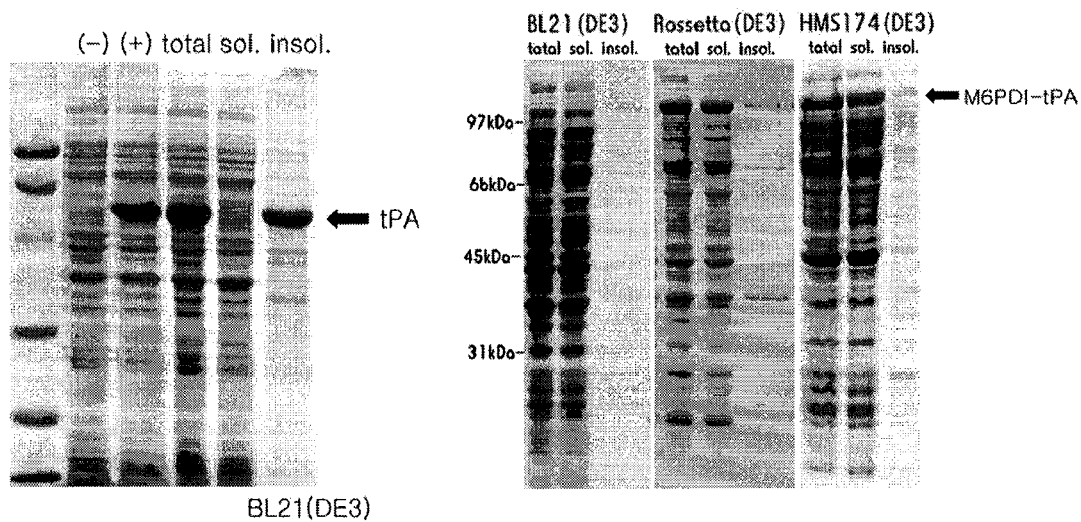
FIG. 4 is an SDS-PAGE diagram showing that all tissue plasminogen activator (tPA) protein is found in an inclusion body (insoluble) only the tPA protein is expressed solely (Left), but a majority of the tPA protein is produced in a soluble form when it is expressed as a fusion protein with a genetically modified M6PDI (Right).

20 ml of the lysed E-coli cell suspension, in which the M6PDI-tPA protein was expressed in a soluble form according to the method described in Embodiment 13, was centrifuged at a rotary speed of 13,000 rpm to separate a supernatant and a precipitate, and then the supernatant and the precipitate were subject to SDS-PAGE to determine whether the M6PDI-tPA protein is expressed in a soluble form (see a right part of FIG. 4). As a result, it was proven that the M6PDI-tPA protein of the present invention is excellent in that the fusion protein is expressed in a soluble form, on the contrary to the fact that all the tPA protein is in an insoluble precipitate fraction when it is expressed solely (see a left part of FIG. 4).

20 ml of the supernatant containing the M6PDI-tPA was filled in a Q-Sepharose cation exchange chromatography column, and then the M6PDI-tPA protein was isolated from the E-coli-derived proteins by allowing 50 mM TrisHCl buffer (pH 8.0) to flow through the column with a linear gradient of 0-0.5 M sodium chloride at a constant flow rate of 0.5 ml/min. TEV protease (0.7 mg/ml) with a histidine tag was added to 20 ml of the M6PDI-tPA-containing fractions as much as 10% of the total reaction solution, and reacted at 4° C. for 16 hours in 50 mM TrisHCl (pH 8.0) buffer to separate tPA protein from the fusion protein (M6PDI), and then Q-Sepharose cation exchange chromatography using isoelectric point differences between the M6PDI and the tPA was carried out in the same manner as described above to purify the tPA protein.

Figure 15:
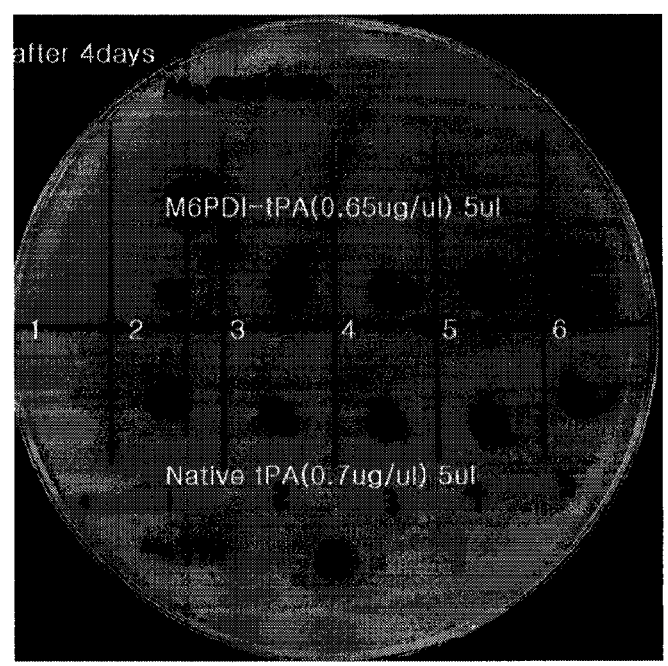
FIG. 15 is a diagram showing comparison between activities of a commercially available wild type tPA and the M6PDI-tPA of the present invention. It might be seen that the M6PDI-tPA of the present invention has a similar activity to the wild type tPA even though it is expressed in a fused form.

Activity of the purified tPA protein was estimated by measuring fibrinolytic activity [Astrup, T. & Mullertz, S. (1952) Arch. Biochem. Biophys. 40: 346-51]. 3 units of human thrombin (Hyphen BioMed) was mixed with human fibrinogen (Hyphen BioMed) dissolved in 10 ml of 50 mM TrisHCl (pH 8.0) solution to a final density of 0.7%, and then carefully poured on a plate without delay and made hard at 4° C. overnight to prepare a fibrin plate. Equivalent amounts (5 to 10 ml) of the purified tPA and a commercially available tPA (Genentech) were spotted on a surface of the plate without its spreading. An activity of the produced tPA was evaluated by comparing to that of the commercially available tPA using a method where the purified tPA and the commercially available tPA were reacted at 37° C. for 6 hours and dissolution areas of their spotted points were measured, respectively. The fibrinolytic activity was measured at an optical density of 600 nm (FIG. 15). As the result of comparing their activities, it was revealed that the tPA protein produced according to the present invention has the same activity as that of the commercially available tPA protein.

Embodiment 15

Purification and Activity of EKL Protein

Figure 5:
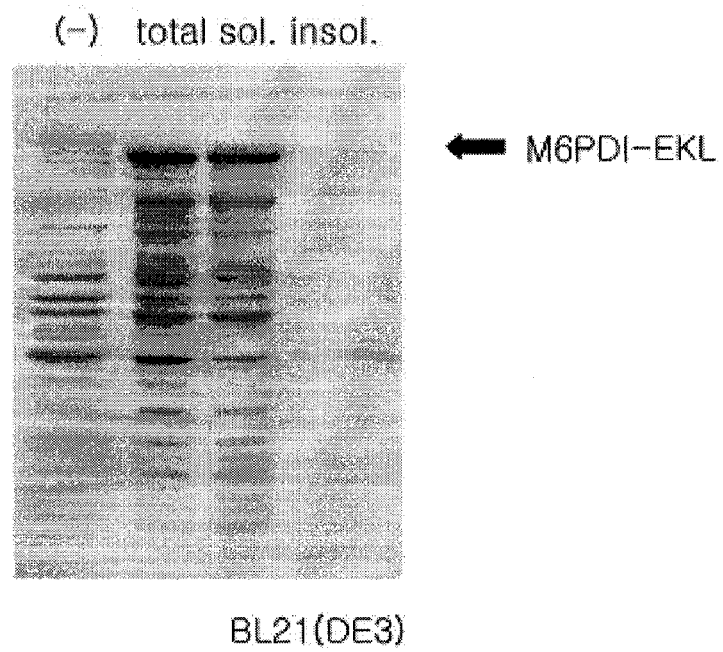
FIG. 5 is an SDS-PAGE diagram showing the total expression level and soluble and insoluble expression levels of the genetically modified M6PDI-EKL fusion protein.

The *E-coli* tranformant, in which the M6PDI-EKL protein prepared in the method of Embodiment 13 is accumulated in a soluble form, was harvested. 400 μml of the culture solution was centrifuged for 10 minutes at a rotary speed of 6,000 rpm to obtain an *E-coli* pellet, and then the *E-coli* pellet was suspended in 20 ml of 50 mM TrisHCl buffer (pH 8.0) and lysed with a sonication method. The cell lysate was centrifuged again to separate a supernatant and a pellet, and then the supernatant and the pellet were subject to SDS-PAGE to determine whether the M6PDI-EKL protein is expressed in a soluble form (FIG. 5).

Figure 6:
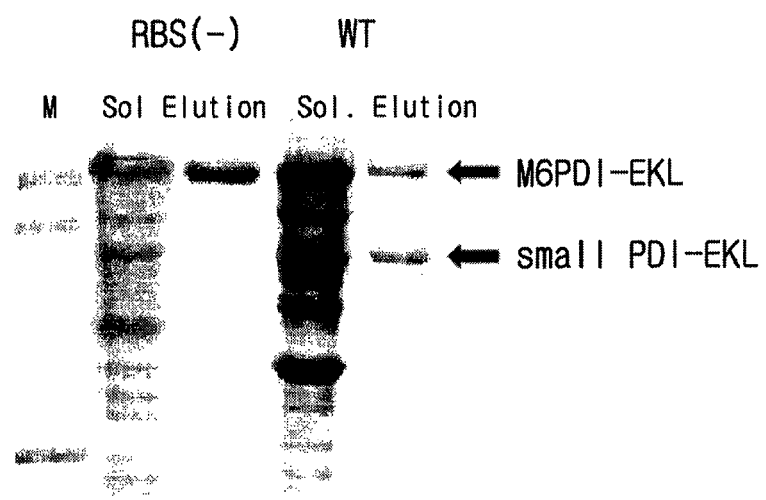
FIG. 6 is an SDS-PAGE diagram after the genetically modified M6PDI-EKL (Left) and the wild type M6PDI-EKL (Right) are expressed and purified using Ni-chelating affinity column chromatography. It was shown that the wild type PDI is co-expressed with small and split PDI-EKL fragments if the wild type PDI is used as a fusion partner.
Figure 7:
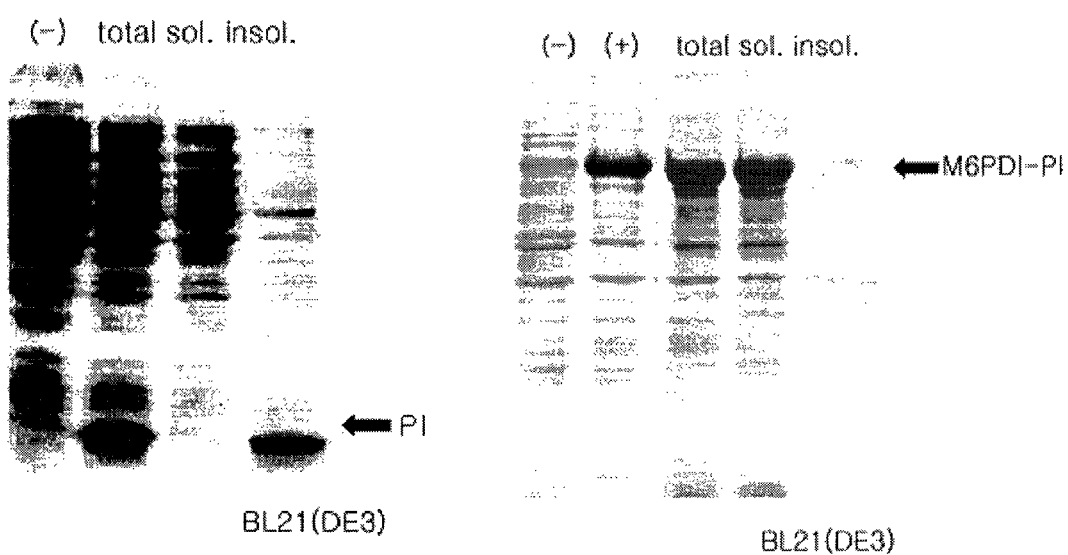
FIG. 7 is an SDS-PAGE diagram showing the total expression levels and soluble and insoluble expression levels of a solely expressed proinsulin (Left) and an M6PDI-proinsulin fusion protein (Right). It is shown that the proinsulin is expressed in a form of an inclusion body when it is expressed solely.
Figure 8:
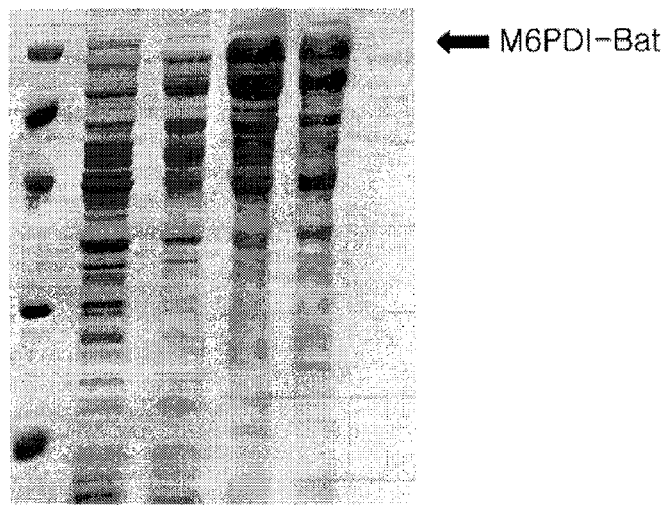
FIG. 8 is an SDS-PAGE diagram showing the total expression level and soluble and insoluble expression levels of an M6PDI-Batroxobin fusion protein.
Figure 9:
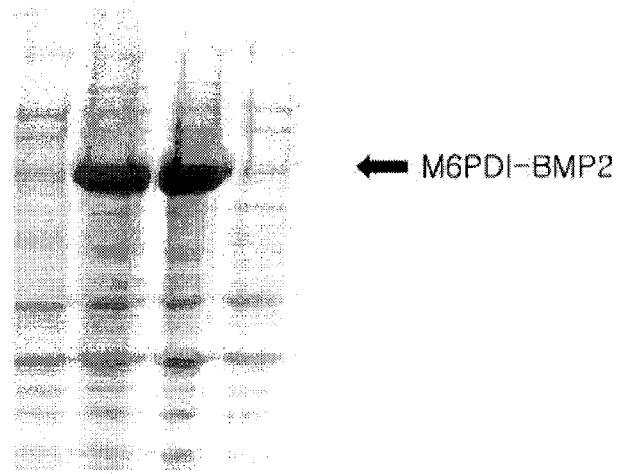
FIG. 9 is an SDS-PAGE diagram showing the total expression level and soluble and insoluble expression levels of an M6PDI-BMP2 fusion protein.
Figure 10:
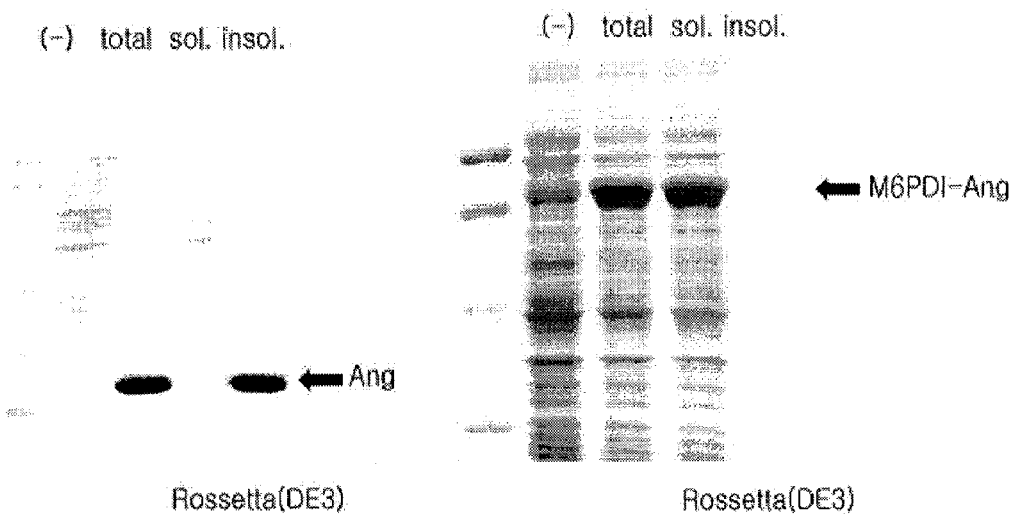
FIG. 10 is an SDS-PAGE diagram showing the total expression levels and soluble and insoluble expression levels of a solely expressed angiogenin and an M6PDI-Angiogenin fusion protein. It is shown that the angiogenin is expressed in a from of an inclusion body when it is expressed solely.
Figure 11:
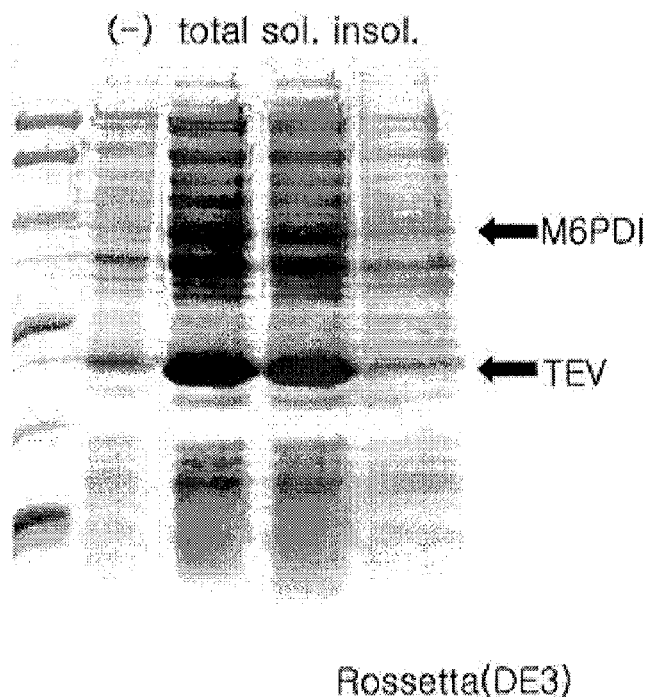
FIG. 11 is an SDS-PAGE diagram showing the total expression level and soluble and insoluble expression levels of an M6PDI-TEV protease fusion protein. It is shown that the M6PDI and the TEV protease are produced in a cleaved form.
Figure 12:
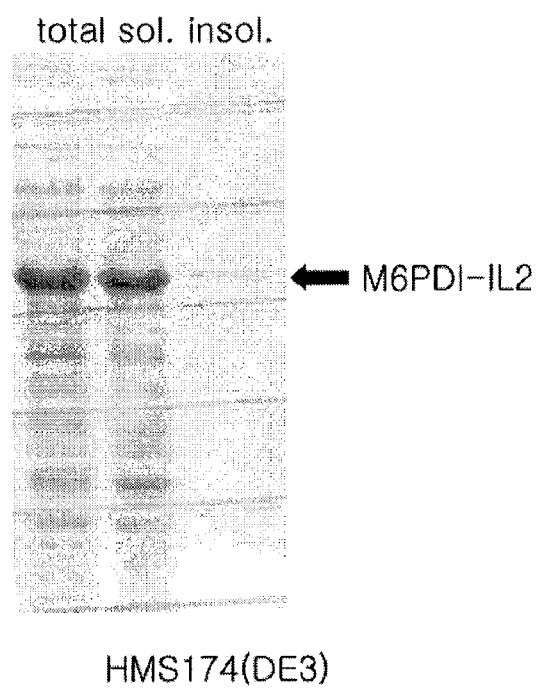
FIG. 12 is an SDS-PAGE diagram showing the total expression levels and soluble and insoluble expression levels of an M6PDI-IL2 fusion protein.
Figure 13:
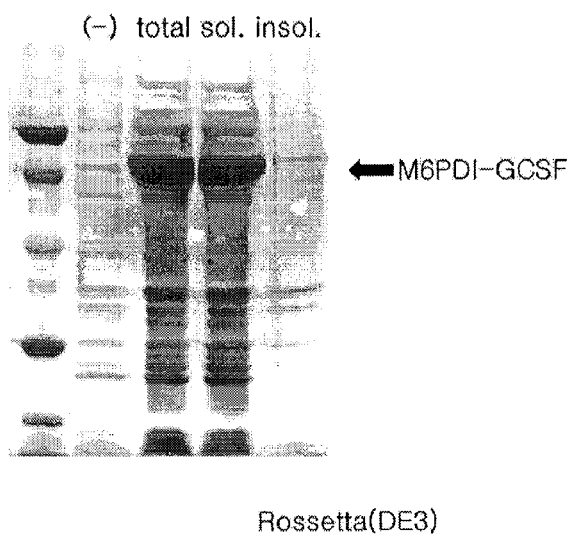
FIG. 13 is an SDS-PAGE diagram showing the total expression levels and soluble and insoluble expression levels of an M6PDI-GCSF fusion protein.
Figure 14:
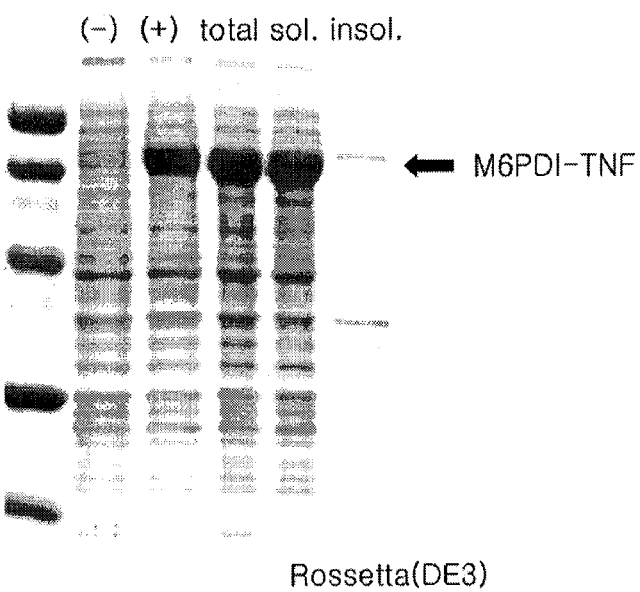
FIG. 14 is an SDS-PAGE diagram showing the total expression levels and soluble and insoluble expression levels of an M6PDI-TNF fusion protein.

In order to determine whether a ribosome binding site is effectively removed, a wild type PDI-EKL and a genetically modified M6PDI-EKL were expressed and purified with Ni-chelating affinity column chromatography, respectively, and then their expression results were compared to determine whether a ribosome binding site is removed (see FIG. 6).

Figure 16:
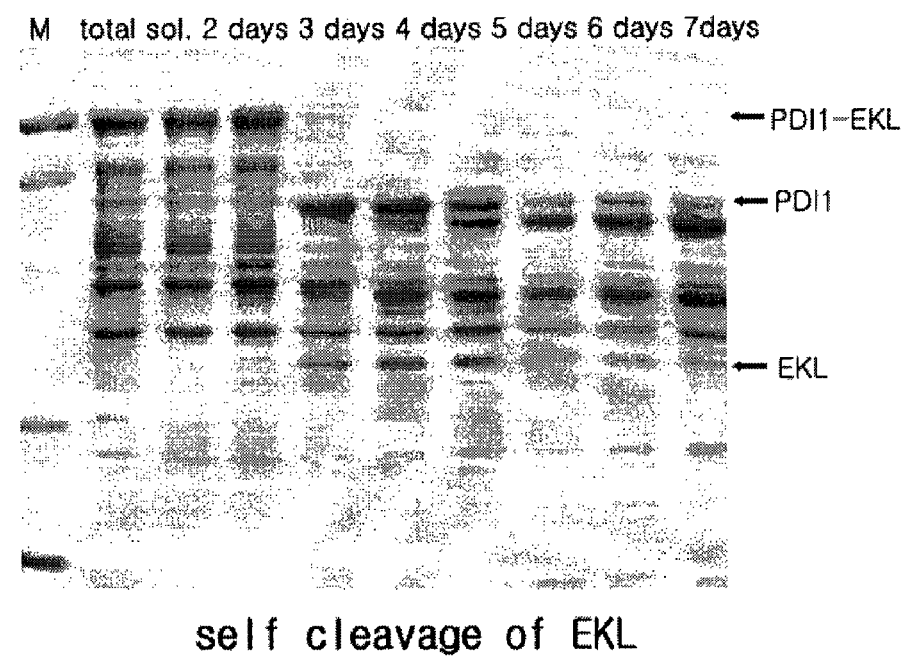
FIG. 16 is a diagram showing that the fusion protein is cleaved into an active enterokinase light chain (EKL) protein with the passage of time.

A carboxyl-terminal domain of amino acid residues (DDDDK (SEQ ID NO: 43)) inserted between the M6PDI and the EKL was self-cleaved to separate the active EKL from the M6PDI by keeping 20 ml of the supernatant containing the M6PDI-EKL at 4° C. for 4 days (FIG. 16). The active EKL was purified with Ni-chelating affinity column chromatography using a histidine tag positioned at carboxyl terminus of the active EKL. The purification conditions are as follows: 20 ml of the supernatant was mixed with 10 ml of nickel-resin in a buffer containing 50 mM TrisHCl (pH 8.0), 500 mM sodium chloride and 10% glycerol, and stirred at 4° C. for 12~16 hours to chelate the EKL with nickel, and the resultant reaction solution was washed with 100 ml, of 10 mM imidazole solution, and then the EKL protein was eluted with a linear gradient of 10-250 mM imidazole solution. 5 ml of a fraction containing the eluted EKL protein was dialyzed at 4° C. in 50 mM TrisHCl (pH 8.0) buffer to remove salts and imidazole from the solution.

An activity of the EKL purified in the present invention was compared with that of the commercially available EKL product (Invitrogen). Glycine-aspartic acid-aspartic acid-aspartic acid-aspartic acid-lysine-beta-naphtylamide (GDDDDK-β-naphtylamide (SEQ ID NO: 45), Sigma) was used as a substrate, and 0.1~2 μg of the EKL protein was added to 400 μl of a buffer (pH 8.0) containing 0.5 mM substrate, 10 mM calcium chloride, 10% DMSO and 25 mM TrisHCl, and then the resultant mixture was excited at 337 nm while its being reacted at 30° C. for 1 minute, and its emission fluorescence was measured at 420 nm. As the result of measuring activity, it was shown that the EKL protein of the present invention has the same activity as that of the commercially available EKL product.

TABLE 1

| Sample | ΔAU/ng |
|---|---|
| EKL from Invitrogen | 0.2 |
| EKL of the present invention | 0.2 |

Embodiment 16

Purification and Activity of Angiogenin

The *E-coli* tranformant, in which the M6PDI-Ang protein prepared in the method of Embodiment 13 is accumulated in a soluble form, was harvested. 400 μml of the culture solution was centrifuged for 10 minutes at a rotary speed of 6,000 rpm to obtain an *E-coli* pellet, and then the *E-coli* pellet was suspended in 30 ml of 30 mM TrisHCl buffer (pH 8.0) containing 300 mM sodium chloride and lysed with a sonication method. The cell lysate was centrifuged for 10 minutes at a rotary speed of 13,000 rpm again to separate a supernatant and a pellet, and then the supernatant containing the M6PDI-Ang protein was purified with Ni-chelating affinity column chromatography using a histidine tag. The purification conditions are as follows: 30 ml of the supernatant was mixed with 15 ml of nickel-resin in a buffer containing 30 mM TrisHCl (pH 8.0) and 300 mM sodium chloride, and stirred at 4° C. for 12~16 hours to chelate the EKL with nickel, and the resultant reaction solution was washed with 150 ml of 40 mM imidazole solution, and then the M6PDI-Ang protein was eluted with a linear gradient of 40-80 mM imidazole solution. A fraction containing the eluted M6PDI-Ang protein was dialyzed at 4° C. in 30 mM TrisHCl (pH 8.0) buffer to remove salts and imidazole from the solution.

A histidine-tagged TEV protease (0.7 mg/ml) was added to a reaction solution as much as 4% of the total reaction solution, reacted at 22° C. for 22 hours in 30 mM TrisHCl (pH 8.0) buffer to cleave a fusion partner (M6PDI) from angiogenin, and then finally purified with high performance liquid chromatography (HPLC). A column, ZORBAX SIL (C8) (Agilent), was used in the high performance liquid chromatography, the purification conditions are as follows: 85% of solution A (99.9% $H_2O$, 0.1% TFA) and 15% of solution B (99.9% Acetonitrile, 0.1% TFA) flow through the column for 15 minutes at a constant flow rate of 0.8 ml/min, and then the solution B flow through the column for 120 minutes with a linear gradient from 15% to 29% to separate angiogenin.

Figure 17:
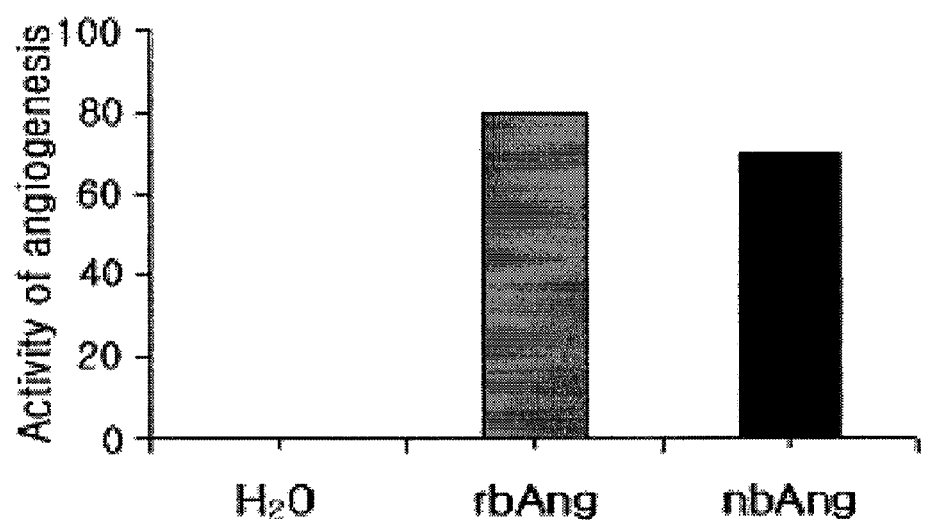
FIG. 17 is a bar graph showing comparison between activities of recombinant angiogenin (rbAng) produced according to the present invention and wild type angiogenin (nbAng) purified from cow mil. It might be seen that the recombinant angiogenin has a better activity than that of the wild type angiogenin.

An activity of the purified recombinant angiogenin was compared with that of the wild type angiogenin isolated from milk. The angiogenin activity was measured using a chick chorioallantoic membrane (CAM) model [Nguyen, M. et al. (1994) Microvasc. Res. 47: 31-40]. As the result of measuring activity, it was shown that the angiogenin prepared in the present invention has the more excellent activity than that of the wild type angiogenin (FIG. 17).

INDUSTRIAL APPLICABILITY

As described above, the method for preparing a recombinant protein according to the present invention may be useful to solve the problems caused in producing the fusion partner in an *E-coli* system, for example a low solubility and a low production of active proteins, and be also widely used for protein drug and industrial protein production by satisfying an improved expression rate of a target protein, an enhanced production of soluble proteins, and protein folding into an active form using a genetically modified PDI as a fusion partner.

What is claimed is:

1. A method for preparing a recombinant protein that improves productivity, solubility and folding of a target protein, the method comprising:
   (a) inserting into a vector a gene encoding protein disulfide isomerase (PDI) as a fusion partner; and
   (b) ligating a gene encoding the target protein with said gene encoding PDI, wherein the amino-terminal domain of said PDI comprises a sequence of 6 amino acid residues KIEEGK (SEQ ID NO: 37) obtained from an amino-terminal domain of a maltose-binding protein, and wherein the recombinant protein comprises a sequence of 6 to 10 histidines at the amino-terminus or carboxy-terminus of the PDI protein, and a peptide sequence consisting of 6 to 10 aspartic acid and glutamic acid residues between said PDI and the target protein.

2. The method for preparing a recombinant protein according to claim 1, wherein the PDI protein is encoded by a gene sequence set forth in SEQ ID NO: 25.

3. The method for preparing a recombinant protein according to claim 1, wherein the target protein is selected from the group consisting of tissue-type plasminogen activator.

4. The method for preparing a recombinant protein according to claim 3, wherein the tissue-type plasminogen activator has the amino acid sequence of SEQ ID NO: 27.

5. The method for preparing a recombinant protein according to claim 1 further comprising a step of transforming a host cell with a recombinant expression vector containing a fused gene in which the gene encoding the target protein is ligated with the gene encoding the PDI.

6. The method for preparing a recombinant protein according to claim 5, wherein the recombinant expression vector is selected from the group consisting of pSSB-PDI1-tPA.

7. The method for preparing a recombinant protein according to claim 5, wherein the host cell is *Escherichia coli*.

8. The method for preparing a recombinant protein according to claim 7, wherein the host cell is a strain *E-coli* KCCM-10646P transformed with the expression vector pSSB-PDI1-tPA.

9. A recombinant protein prepared according to the method as defined in claim 1.

10. A nucleic acid comprising a nucleotide sequence encoding a fusion protein comprising protein disulfide isomerase ligated to a target protein; wherein the amino-terminal domain of said PDI comprises a sequence of 6 amino acid residues KIEEGK (SEQ ID NO: 37) obtained from an amino-terminal domain of a maltose-binding protein; wherein the recombinant protein comprises a sequence of 6 to 10 histidines at the amino-terminus or carboxy-terminus of the PDI protein, and a peptide sequence consisting of 6 to 10 aspartic acid and glutamic acid residues between said PDI and the target protein.

11. A recombinant expression vector comprising the nucleic acid of claim 10.

12. A host cell transformed with the recombinant expression vector of claim 11.

* * * * *

```
                        SEQUENCE LISTING

<160> NUMBER OF SEQ ID NOS: 45

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
catatgaaaa tcgaagaagg taaagacgct ctggaggagg ag                          42

<210> SEQ ID NO 2
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggtaccgccg ccaccgcctt catcatcatc ttcatccagt tcatccttca cggc            54

<210> SEQ ID NO 3
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgtgcggctt attacccttg atgaagatat gaccaagtac aaaccg                     46

<210> SEQ ID NO 4
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cggtttgtac ttggtcatat cttcatcaag ggtaataagc cgcaca                     46

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggtaccgaga acctgtactt ccaatcttac caagtgatct gccgc                      45
```

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtcgacttat cacggtcgca tgttgtcacg aat                                    33

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgcggtaccg acgatgatga caagattgtc ggaggaagct cc                          42

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgggtcgact tactagtgat ggtgatggtg atgaaa                                 36

<210> SEQ ID NO 9
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggtacccatc atcaccatca tcaccatcac cgtcgtttcg ttaatcagca cctgtgcggc       60
tctcac                                                                  66

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtcgacttac tagttacaat agtt                                              24

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggtaccgaga acctgtactt ccaagtcatt gga                                    33

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtcgacttac tacgggcaag tcgcagtt                                        28

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggtaccgaga acctgtactt ccaacaagcc aaacacaaac ag                        42

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtcgactcac tagcgacacc cacaacc                                         27

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggtaccgaaa atctttactt ccaagctcaa gattac                               36

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gaatgcggat ccgtcgactt actagtggcg tggagt                               36

<210> SEQ ID NO 17
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggtaccgaaa atctttactt ccaaggttcc ttgtttaagg ga                        42

<210> SEQ ID NO 18

```
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gtcgacctat taatggtggt gatgatggtg gtggtggtca cgatgaattc            50

<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggcggtaccg aaaatcttta cttccaagca cctacttca                        39

<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gaatgcggat ccgtcgactt actataaagt tagtgt                           36

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggtaccgaga acctgtactt ccaaacccccc ctgggccctg ccagc                45

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtcgacctat cagggctggg caag                                        24

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggtaccgaaa atctttactt ccaaggtgtc agatcatctt ctcga                 45

<210> SEQ ID NO 24
<211> LENGTH: 27
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 24
gtcgacttat cacagggcaa tgatccc                                        27

<210> SEQ ID NO 25
<211> LENGTH: 1467
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25
gacgctctgg aggaggagga caacgtcctg gtgctgaaga gagcaacttt cgcagagccg      60
gcggcgcaca actacctgct ggtggagttc tatgccccat ggtgtggcca ctgcaaagca     120
ctggccccag agtatgccaa agctgctgca aaactgaagg cagaaggctc tgagatccga     180
ctagcaaagg tggacgccac agaagagtct gacctggccc agcagtatgg tgtccgtggc     240
taccccacaa tcaagttctt caagaatgga gacacagcct ccccaaagga atatacagct     300
ggcagggaag ctgacgacat tgtgaactgg ctgaagaaac gcacaggccc agcagccaca     360
accctgtctg acactgcagc tgcagagtcc ttggtggact caagcgaagt gacggtcatc     420
ggcttcttca aggacgcagg gtcagactcc gccaagcagt tcttgctggc agcagaggct     480
gttgatgaca taccttttgg aatcacttcc aatagcgatg tgttttccaa gtaccagctg     540
gacaaggatg gggtggtcct ctttaagaag tttgatgaag ccgcaacaa ttttgaaggt     600 gagatcacca aggagaagct attagacttc atcaagcaca ccagctgcc tttggtcatc     660 gagttcactg aacagacagc tccaaagatt tcggaggtg aaatcaagac acatattctg     720
ctgttcctgc ccaagagtgt gtctgactac gatggcaaat tgagcaactt taagaaagcg     780
gccgagggct ttaagggcaa gatcctgttc atcttcatcg atagtgacca cactgacaac     840
cagcgcatac ttgagttctt tggcctgaag aaggaggaat gtccagctgt gcggcttatt     900
acccttgatg aagatatgac caagtacaaa ccggagtcag acgagctgac agctgagaag     960
atcacacaat tttgccacca cttcctggag ggcaagatca gccccacct gatgagccag    1020 gaactgcctg aagactggga caagcagcca gtgaaagtgc tagttgggaa aaactttgag    1080
gaggttgctt ttgatgagaa aaagaacgtg tttgttgaat tctatgctcc ctggtgtggt    1140
cactgcaagc agctagcccc gatttgggat aaactgggag agacatacaa agaccatgag    1200
aatatcgtca tcgctaagat ggactcaaca gccaatgagg tggaagctgt gaaggtgcac    1260
agctttccca cactcaagtt cttcccagca agtgcagaca gaacggtcat tgattacaac    1320
ggtgagcgga cactagatgg ttttaagaaa ttcttggaga gcggtggcca ggatggagcg    1380
ggggacaatg acgacctcga cctagaagaa gctttagagc cagatatgga agaagacgac    1440
gatcagaaag ccgtgaagga tgaactg                                       1467

<210> SEQ ID NO 26
<211> LENGTH: 501
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

```
Asp Ala Leu Glu Glu Glu Asp Asn Val Leu Val Leu Lys Lys Ser Asn
  1               5                  10                  15

Phe Ala Glu Pro Ala Ala His Asn Tyr Leu Leu Val Glu Phe Tyr Ala
             20                  25                  30

Pro Trp Cys Gly His Cys Lys Ala Leu Ala Pro Glu Tyr Ala Lys Ala
         35                  40                  45

Ala Ala Lys Leu Lys Ala Glu Gly Ser Glu Ile Arg Leu Ala Lys Val
 50                  55                  60

Asp Ala Thr Glu Glu Ser Asp Leu Ala Gln Gln Tyr Gly Val Arg Gly
 65                  70                  75                  80

Tyr Pro Thr Ile Lys Phe Phe Lys Asn Gly Asp Thr Ala Ser Pro Lys
                 85                  90                  95

Glu Tyr Thr Ala Gly Arg Glu Ala Asp Asp Ile Val Asn Trp Leu Lys
            100                 105                 110

Lys Arg Thr Gly Pro Ala Ala Thr Thr Leu Ser Asp Thr Ala Ala Ala
        115                 120                 125

Glu Ser Leu Val Asp Ser Ser Glu Val Thr Val Ile Gly Phe Phe Lys
130                 135                 140

Asp Ala Gly Ser Asp Ser Ala Lys Gln Phe Leu Leu Ala Ala Glu Ala
145                 150                 155                 160

Val Asp Asp Ile Pro Phe Gly Ile Thr Ser Asn Ser Asp Val Phe Ser
                165                 170                 175

Lys Tyr Gln Leu Asp Lys Asp Gly Val Val Leu Phe Lys Lys Phe Asp
            180                 185                 190

Glu Gly Arg Asn Asn Phe Glu Gly Glu Ile Thr Lys Glu Lys Leu Leu
        195                 200                 205

Asp Phe Ile Lys His Asn Gln Leu Pro Leu Val Ile Glu Phe Thr Glu
210                 215                 220

Gln Thr Ala Pro Lys Ile Phe Gly Gly Glu Ile Lys Thr His Ile Leu
225                 230                 235                 240

Leu Phe Leu Pro Lys Ser Val Ser Asp Tyr Asp Gly Lys Leu Ser Asn
                245                 250                 255

Phe Lys Lys Ala Ala Glu Gly Phe Lys Gly Lys Ile Leu Phe Ile Phe
            260                 265                 270

Ile Asp Ser Asp His Thr Asp Asn Gln Arg Ile Leu Glu Phe Phe Gly
        275                 280                 285

Leu Lys Lys Glu Glu Cys Pro Ala Val Arg Leu Ile Thr Leu Asp Glu
290                 295                 300

Asp Met Thr Lys Tyr Lys Pro Glu Ser Asp Glu Leu Thr Ala Glu Lys
305                 310                 315                 320

Ile Thr Gln Phe Cys His His Phe Leu Glu Gly Lys Ile Lys Pro His
                325                 330                 335

Leu Met Ser Gln Glu Leu Pro Glu Asp Trp Asp Lys Gln Pro Val Lys
            340                 345                 350

Val Leu Val Gly Lys Asn Phe Glu Glu Val Ala Phe Asp Glu Lys Lys
        355                 360                 365

Asn Val Phe Val Glu Phe Tyr Ala Pro Trp Cys Gly His Cys Lys Gln
370                 375                 380

Leu Ala Pro Ile Trp Asp Lys Leu Gly Glu Thr Tyr Lys Asp His Glu
385                 390                 395                 400

Asn Ile Val Ile Ala Lys Met Asp Ser Thr Ala Asn Glu Val Glu Ala
                405                 410                 415

Val Lys Val His Ser Phe Pro Thr Leu Lys Phe Phe Pro Ala Ser Ala
```

```
                        420                 425                 430
Asp Arg Thr Val Ile Asp Tyr Asn Gly Glu Arg Thr Leu Asp Gly Phe
            435                 440                 445

Lys Lys Phe Leu Glu Ser Gly Gly Gln Asp Gly Ala Gly Asp Asn Asp
        450                 455                 460

Asp Leu Asp Leu Glu Glu Ala Leu Glu Pro Asp Met Glu Glu Asp Asp
465                 470                 475                 480

Asp Gln Lys Ala Val Lys Asp Glu Leu Asp Glu Asp Asp Glu Gly
            485                 490                 495

Gly Gly Gly Gly Thr
            500

<210> SEQ ID NO 27
<211> LENGTH: 533
<212> TYPE: PRT
<213> ORGANISM: Homo sapiens

<400> SEQUENCE: 27

Glu Asn Leu Tyr Phe Gln Ser Tyr Gln Val Ile Cys Arg Asp Glu Lys
1               5                   10                  15

Thr Gln Met Ile Tyr Gln Gln His Gln Ser Trp Leu Arg Pro Val Leu
            20                  25                  30

Arg Ser Asn Arg Val Glu Tyr Cys Trp Cys Asn Ser Gly Arg Ala Gln
        35                  40                  45

Cys His Ser Val Pro Val Lys Ser Cys Ser Glu Pro Arg Cys Phe Asn
    50                  55                  60

Gly Gly Thr Cys Gln Gln Ala Leu Tyr Phe Ser Asp Phe Val Cys Gln
65                  70                  75                  80

Cys Pro Glu Gly Phe Ala Gly Lys Cys Cys Glu Ile Asp Thr Arg Ala
                85                  90                  95

Thr Cys Tyr Glu Asp Gln Gly Ile Ser Tyr Arg Gly Thr Trp Ser Thr
            100                 105                 110

Ala Glu Ser Gly Ala Glu Cys Thr Asn Trp Asn Ser Ser Ala Leu Ala
        115                 120                 125

Gln Lys Pro Tyr Ser Gly Arg Arg Pro Asp Ala Ile Arg Leu Gly Leu
    130                 135                 140

Gly Asn His Asn Tyr Cys Arg Asn Pro Asp Arg Asp Ser Lys Pro Trp
145                 150                 155                 160

Cys Tyr Val Phe Lys Ala Gly Lys Tyr Ser Ser Glu Phe Cys Ser Thr
                165                 170                 175

Pro Ala Cys Ser Glu Gly Asn Ser Asp Cys Tyr Phe Gly Asn Gly Ser
            180                 185                 190

Ala Tyr Arg Gly Thr His Ser Leu Thr Glu Ser Gly Ala Ser Cys Leu
        195                 200                 205

Pro Trp Asn Ser Met Ile Leu Ile Gly Lys Val Tyr Thr Ala Gln Asn
    210                 215                 220

Pro Ser Ala Gln Ala Leu Gly Leu Gly Lys His Asn Tyr Cys Arg Asn
225                 230                 235                 240

Pro Asp Gly Asp Ala Lys Pro Trp Cys His Val Leu Lys Asn Arg Arg
                245                 250                 255

Leu Thr Trp Glu Tyr Cys Asp Val Pro Ser Cys Ser Thr Cys Gly Leu
            260                 265                 270

Arg Gln Tyr Ser Gln Pro Gln Phe Arg Ile Lys Gly Gly Leu Phe Ala
        275                 280                 285

Asp Ile Ala Ser His Pro Trp Gln Ala Ala Ile Phe Ala Lys His Arg
```

```
                    290                 295                 300
Arg Ser Pro Gly Glu Arg Phe Leu Cys Gly Gly Ile Leu Ile Ser Ser
305                 310                 315                 320

Cys Trp Ile Leu Ser Ala Ala His Cys Phe Gln Glu Arg Phe Pro Pro
                325                 330                 335

His His Leu Thr Val Ile Leu Gly Arg Thr Tyr Arg Val Val Pro Gly
            340                 345                 350

Glu Glu Glu Gln Lys Phe Glu Val Glu Lys Tyr Ile Val His Lys Glu
        355                 360                 365

Phe Asp Asp Asp Thr Tyr Asp Asn Asp Ile Ala Leu Leu Gln Leu Lys
    370                 375                 380

Ser Asp Ser Ser Arg Cys Ala Gln Glu Ser Ser Val Val Arg Thr Val
385                 390                 395                 400

Cys Leu Pro Pro Ala Asp Leu Gln Leu Pro Asp Trp Thr Glu Cys Glu
                405                 410                 415

Leu Ser Gly Tyr Gly Lys His Glu Ala Leu Ser Pro Phe Tyr Ser Glu
            420                 425                 430

Arg Leu Lys Glu Ala His Val Arg Leu Tyr Pro Ser Ser Arg Cys Thr
        435                 440                 445

Ser Gln His Leu Leu Asn Arg Thr Val Thr Asp Asn Met Leu Cys Ala
    450                 455                 460

Gly Asp Thr Arg Ser Gly Gly Pro Gln Ala Asn Leu His Asp Ala Cys
465                 470                 475                 480

Gln Gly Asp Ser Gly Gly Pro Leu Val Cys Leu Asn Asp Gly Arg Met
                485                 490                 495

Thr Leu Val Gly Ile Ile Ser Trp Gly Leu Gly Cys Gly Gln Lys Asp
            500                 505                 510

Val Pro Gly Val Tyr Thr Lys Val Thr Asn Tyr Leu Asp Trp Ile Arg
        515                 520                 525

Asp Asn Met Arg Pro
    530

<210> SEQ ID NO 28
<211> LENGTH: 245
<212> TYPE: PRT
<213> ORGANISM: Bos sp.

<400> SEQUENCE: 28

Asp Asp Asp Asp Lys Ile Val Gly Gly Ser Asp Ser Arg Glu Gly Ala
1               5                   10                  15

Trp Pro Trp Val Val Ala Leu Tyr Phe Asp Asp Gln Gln Val Cys Gly
            20                  25                  30

Ala Ser Leu Val Ser Arg Asp Trp Leu Val Ser Ala Ala His Cys Val
        35                  40                  45

Tyr Gly Arg Asn Met Glu Pro Ser Lys Trp Lys Ala Val Leu Gly Leu
    50                  55                  60

His Met Ala Ser Asn Leu Thr Ser Pro Gln Ile Glu Thr Arg Leu Ile
65                  70                  75                  80

Asp Gln Ile Val Ile Asn Pro His Tyr Asn Lys Arg Arg Lys Asn Asn
                85                  90                  95

Asp Ile Ala Met Met His Leu Glu Met Lys Val Asn Tyr Thr Asp Tyr
            100                 105                 110

Ile Gln Pro Ile Cys Leu Pro Glu Glu Asn Gln Val Phe Pro Pro Gly
        115                 120                 125

Arg Ile Cys Ser Ile Ala Gly Trp Gly Ala Leu Ile Tyr Gln Gly Ser
```

```
                130              135               140
Thr Ala Asp Val Leu Gln Glu Ala Asp Val Pro Leu Leu Ser Asn Glu
145                 150                 155                 160

Lys Cys Gln Gln Gln Met Pro Glu Tyr Asn Ile Thr Glu Asn Met Val
                165                 170                 175

Cys Ala Gly Tyr Glu Ala Gly Gly Val Asp Ser Cys Gln Gly Asp Ser
                180                 185                 190

Gly Gly Pro Leu Met Cys Gln Glu Asn Asn Arg Trp Leu Leu Ala Gly
                195                 200                 205

Val Thr Ser Phe Gly Tyr Gln Cys Ala Leu Pro Asn Arg Pro Gly Val
                210                 215                 220

Tyr Ala Arg Val Pro Arg Phe Thr Glu Trp Ile Gln Ser Phe Leu His
225                 230                 235                 240

His His His His His
                245

<210> SEQ ID NO 29
<211> LENGTH: 96
<212> TYPE: PRT
<213> ORGANISM: Homo sapiens

<400> SEQUENCE: 29

His His His His His His His Arg Arg Phe Val Asn Gln His Leu
1               5                   10                  15

Cys Gly Ser His Leu Val Glu Ala Leu Tyr Leu Val Cys Gly Glu Arg
                20                  25                  30

Gly Phe Phe Tyr Thr Pro Lys Thr Arg Arg Glu Ala Glu Asp Leu Gln
            35                  40                  45

Val Gly Gln Val Glu Leu Gly Gly Pro Gly Ala Gly Ser Leu Gln
    50                  55                  60

Pro Leu Ala Leu Glu Gly Ser Leu Gln Lys Arg Gly Ile Val Glu Gln
65                  70                  75                  80

Cys Cys Thr Ser Ile Cys Ser Leu Tyr Gln Leu Glu Asn Tyr Cys Asn
                85                  90                  95

<210> SEQ ID NO 30
<211> LENGTH: 237
<212> TYPE: PRT
<213> ORGANISM: Bothrops atrox

<400> SEQUENCE: 30

Glu Asn Leu Tyr Phe Gln Val Ile Gly Gly Asp Glu Cys Asp Ile Asn
1               5                   10                  15

Glu His Pro Phe Leu Ala Phe Met Tyr Tyr Ser Pro Arg Tyr Phe Cys
                20                  25                  30

Gly Met Thr Leu Ile Asn Gln Glu Trp Val Leu Thr Ala Ala His Cys
            35                  40                  45

Asn Arg Arg Phe Met Arg Ile His Leu Gly Lys His Ala Gly Ser Val
    50                  55                  60

Ala Asn Tyr Asp Glu Val Val Arg Tyr Pro Lys Glu Lys Phe Ile Cys
65                  70                  75                  80

Pro Asn Lys Lys Lys Asn Val Ile Thr Asp Lys Asp Ile Met Leu Ile
                85                  90                  95

Arg Leu Asp Arg Pro Val Lys Asn Ser Glu His Ile Ala Pro Leu Ser
                100                 105                 110

Leu Pro Ser Asn Pro Pro Ser Val Gly Ser Val Cys Arg Ile Met Gly
                115                 120                 125
```

```
Trp Gly Ala Ile Thr Thr Ser Glu Asp Thr Tyr Pro Asp Val Pro His
    130                 135                 140

Cys Ala Asn Ile Asn Leu Phe Asn Asn Thr Val Cys Arg Glu Ala Tyr
145                 150                 155                 160

Asn Gly Leu Pro Ala Lys Thr Leu Cys Ala Gly Val Leu Gln Gly Gly
                165                 170                 175

Ile Asp Thr Cys Gly Gly Asp Ser Gly Gly Pro Leu Ile Cys Asn Gly
            180                 185                 190

Gln Phe Gln Gly Ile Leu Ser Trp Gly Ser Asp Pro Cys Ala Glu Pro
        195                 200                 205

Arg Lys Pro Ala Phe Tyr Thr Lys Val Phe Asp Tyr Leu Pro Trp Ile
    210                 215                 220

Gln Ser Ile Ile Ala Gly Asn Lys Thr Ala Thr Cys Pro
225                 230                 235
```

<210> SEQ ID NO 31
<211> LENGTH: 120
<212> TYPE: PRT
<213> ORGANISM: Homo sapiens

<400> SEQUENCE: 31

```
Glu Asn Leu Tyr Phe Gln Gln Ala Lys His Lys Gln Arg Lys Arg Leu
1               5                   10                  15

Lys Ser Ser Cys Lys Arg His Pro Leu Tyr Val Asp Phe Ser Asp Val
                20                  25                  30

Gly Trp Asn Asp Trp Ile Val Ala Pro Pro Gly Tyr His Ala Phe Tyr
            35                  40                  45

Cys His Gly Glu Cys Pro Phe Pro Leu Ala Asp His Leu Asn Ser Thr
        50                  55                  60

Asn His Ala Ile Val Gln Thr Leu Val Asn Ser Val Asn Ser Lys Ile
65                  70                  75                  80

Pro Lys Ala Cys Cys Val Pro Thr Glu Leu Ser Ala Ile Ser Met Leu
                85                  90                  95

Tyr Leu Asp Glu Asn Glu Lys Val Val Leu Lys Asn Tyr Gln Asp Met
                100                 105                 110

Val Val Glu Gly Cys Gly Cys Arg
            115                 120
```

<210> SEQ ID NO 32
<211> LENGTH: 131
<212> TYPE: PRT
<213> ORGANISM: Bos sp.

<400> SEQUENCE: 32

```
Glu Asn Leu Tyr Phe Gln Ala Gln Asp Asp Tyr Arg Tyr Ile His Phe
1               5                   10                  15

Leu Thr Gln His Tyr Asp Ala Lys Pro Lys Gly Arg Asn Asp Glu Tyr
                20                  25                  30

Cys Phe Asn Met Met Lys Asn Arg Arg Leu Thr Arg Pro Cys Lys Asp
            35                  40                  45

Arg Asn Thr Phe Ile His Gly Asn Lys Asn Asp Ile Lys Ala Ile Cys
        50                  55                  60

Glu Asp Arg Asn Gly Gln Pro Tyr Arg Gly Asp Leu Arg Ile Ser Lys
65                  70                  75                  80

Ser Glu Phe Gln Ile Thr Ile Cys Lys His Lys Gly Gly Ser Ser Arg
                85                  90                  95
```

```
Pro Pro Cys Arg Tyr Gly Ala Thr Glu Asp Ser Arg Val Ile Val Val
            100                 105                 110

Gly Cys Glu Asn Gly Leu Pro Val His Phe Asp Glu Ser Phe Ile Thr
            115                 120                 125

Pro Arg His
    130

<210> SEQ ID NO 33
<211> LENGTH: 260
<212> TYPE: PRT
<213> ORGANISM: Tobacco etch virus

<400> SEQUENCE: 33

Glu Asn Leu Tyr Phe Gln Gly Ser Leu Phe Lys Gly Pro Arg Asp Tyr
 1               5                  10                  15

Asn Pro Ile Ser Ser Thr Ile Cys His Leu Thr Asn Glu Ser Asp Gly
            20                  25                  30

His Thr Thr Ser Leu Tyr Gly Ile Gly Phe Gly Pro Phe Ile Ile Thr
            35                  40                  45

Asn Lys His Leu Phe Arg Arg Asn Asn Gly Thr Leu Leu Val Gln Ser
     50                  55                  60

Leu His Gly Val Phe Lys Val Lys Asn Thr Thr Thr Leu Gln Gln His
 65                  70                  75                  80

Leu Ile Asp Gly Arg Asp Met Ile Ile Ile Arg Met Pro Lys Asp Phe
                 85                  90                  95

Pro Pro Phe Pro Gln Lys Leu Lys Phe Arg Glu Pro Gln Arg Glu Glu
            100                 105                 110

Arg Ile Cys Leu Val Thr Thr Asn Phe Gln Thr Lys Ser Met Ser Ser
            115                 120                 125

Met Val Ser Asp Thr Ser Cys Thr Phe Pro Ser Ser Asp Gly Ile Phe
130                 135                 140

Trp Lys His Trp Ile Gln Thr Lys Asp Gly Gln Cys Gly Ser Pro Leu
145                 150                 155                 160

Val Ser Thr Arg Asp Gly Phe Ile Val Gly Ile His Ser Ala Ser Asn
                165                 170                 175

Phe Thr Asn Thr Asn Asn Tyr Phe Thr Ser Val Pro Lys Asn Phe Met
            180                 185                 190

Glu Leu Leu Thr Ser Gln Glu Ala Gln Gln Trp Val Ser Gly Trp Arg
            195                 200                 205

Leu Asn Ala Asp Ser Val Leu Trp Gly Gly His Lys Val Phe Met Ser
     210                 215                 220

Lys Pro Glu Glu Pro Phe Gln Pro Val Lys Glu Ala Thr Gln Leu Met
225                 230                 235                 240

Asn Glu Leu Val Tyr Ser Pro Gly Ile His Arg Asp His His His His
                245                 250                 255

His His His His
        260

<210> SEQ ID NO 34
<211> LENGTH: 140
<212> TYPE: PRT
<213> ORGANISM: Homo sapiens

<400> SEQUENCE: 34

Glu Asn Leu Tyr Phe Gln Ala Pro Thr Ser Thr Ser Thr Lys Lys Thr
 1               5                  10                  15

Gln Leu Gln Leu Glu His Leu Leu Leu Asp Leu Gln Met Ile Leu Asn
```

```
                    20                  25                  30
Gly Ile Asn Asn Tyr Lys Asn Pro Lys Leu Thr Arg Met Leu Thr Phe
            35                  40                  45
Lys Phe Tyr Met Pro Lys Lys Ala Thr Glu Leu Lys His Leu Gln Cys
    50                  55                  60
Leu Glu Glu Leu Lys Pro Leu Glu Glu Val Leu Asn Leu Ala Gln
65                  70                  75                  80
Ser Lys Asn Phe His Leu Arg Pro Arg Asp Leu Ile Ser Asn Ile Asn
                85                  90                  95
Val Ile Val Leu Glu Leu Lys Gly Ser Glu Thr Thr Phe Met Cys Glu
            100                 105                 110
Tyr Ala Asp Glu Thr Ala Thr Ile Val Glu Phe Leu Asn Arg Trp Ile
            115                 120                 125
Thr Phe Cys Gln Ser Ile Ile Ser Thr Leu Thr Leu
            130                 135                 140

<210> SEQ ID NO 35
<211> LENGTH: 180
<212> TYPE: PRT
<213> ORGANISM: Homo sapiens

<400> SEQUENCE: 35

Glu Asn Leu Tyr Phe Gln Thr Pro Leu Gly Pro Ala Ser Ser Leu Pro
1               5                   10                  15
Gln Ser Phe Leu Leu Lys Cys Leu Glu Gln Val Arg Lys Ile Gln Gly
            20                  25                  30
Asp Gly Ala Ala Leu Gln Glu Lys Leu Cys Ala Thr Tyr Lys Leu Cys
        35                  40                  45
His Pro Glu Glu Leu Val Leu Leu Gly His Ser Leu Gly Ile Pro Trp
    50                  55                  60
Ala Pro Leu Ser Ser Cys Pro Ser Gln Ala Leu Gln Leu Ala Gly Cys
65                  70                  75                  80
Leu Ser Gln Leu His Ser Gly Leu Phe Leu Tyr Gln Gly Leu Leu Gln
                85                  90                  95
Ala Leu Glu Gly Ile Ser Pro Glu Leu Gly Pro Thr Leu Asp Thr Leu
            100                 105                 110
Gln Leu Asp Val Ala Asp Phe Ala Thr Thr Ile Trp Gln Gln Met Glu
        115                 120                 125
Glu Leu Gly Met Ala Pro Ala Leu Gln Pro Thr Gln Gly Ala Met Pro
    130                 135                 140
Ala Phe Ala Ser Ala Phe Gln Arg Arg Ala Gly Gly Val Leu Val Ala
145                 150                 155                 160
Ser His Leu Gln Ser Phe Leu Glu Val Ser Tyr Arg Val Leu Arg His
                165                 170                 175
Leu Ala Gln Pro
            180

<210> SEQ ID NO 36
<211> LENGTH: 164
<212> TYPE: PRT
<213> ORGANISM: Homo sapiens

<400> SEQUENCE: 36

Glu Asn Leu Tyr Phe Gln Gly Val Arg Ser Ser Arg Thr Pro Ser
1               5                   10                  15
Asp Lys Pro Val Ala His Val Val Ala Asn Pro Gln Ala Glu Gly Gln
            20                  25                  30
```

```
Leu Gln Trp Leu Asn Arg Arg Ala Asn Ala Leu Leu Ala Asn Gly Val
         35                  40                  45

Glu Leu Arg Asp Asn Gln Leu Val Val Pro Ser Gly Leu Tyr Leu
 50                  55                  60

Ile Tyr Ser Gln Val Leu Phe Lys Gly Gln Gly Cys Pro Ser Thr His
 65                  70                  75                  80

Val Leu Leu Thr His Thr Ile Ser Arg Ile Ala Val Ser Tyr Gln Thr
                 85                  90                  95

Lys Val Asn Leu Leu Ser Ala Ile Lys Ser Pro Cys Gln Arg Glu Thr
                100                 105                 110

Pro Glu Gly Ala Glu Ala Lys Pro Trp Tyr Glu Pro Ile Tyr Leu Gly
                115                 120                 125

Gly Val Phe Gln Leu Glu Lys Gly Asp Arg Leu Ser Ala Glu Ile Asn
         130                 135                 140

Arg Pro Asp Tyr Leu Asp Phe Ala Glu Ser Gly Gln Val Tyr Phe Gly
145                 150                 155                 160

Ile Ile Ala Leu

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Lys Ile Glu Glu Gly Lys
1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Glu Asp Asp Asp Glu
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Glu Asp Glu Asp Glu
1               5

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40
```

Asp Glu Asp Glu Asp Glu Asp Glu Asp Glu
1               5                   10

<210> SEQ ID NO 41
<211> LENGTH: 1485
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

| | | | | | |
|---|---|---|---|---|---|
| aaaatcgaag | aaggtaaaga | cgctctggag | gaggaggaca | acgtcctggt | gctgaagaag | 60 |
| agcaacttcg | cagagccggc | ggcgcacaac | tacctgctgg | tggagttcta | tgccccatgg | 120 |
| tgtggccact | gcaaagcact | ggccccagag | tatgccaaag | ctgctgcaaa | actgaaggca | 180 |
| gaaggctctg | agatccgact | agcaaaggtg | gacgccacag | aagagtctga | cctggcccag | 240 |
| cagtatggtg | tccgtggcta | ccccacaatc | aagttcttca | gaatggaga | cacagcctcc | 300 |
| ccaaaggaat | atacagctgg | cagggaagct | gacgacattg | tgaactggct | gaagaaacgc | 360 |
| acaggcccag | cagccacaac | cctgtctgac | actgcagctg | cagagtcctt | ggtggactca | 420 |
| agcgaagtga | cggtcatcgg | cttcttcaag | gacgcagggt | cagactccgc | caagcagttc | 480 |
| ttgctggcag | cagaggctgt | tgatgacata | ccttttggaa | tcacttccaa | tagcgatgtg | 540 |
| ttttccaagt | accagctgga | caaggatggg | gtggtcctct | ttaagaagtt | tgatgaaggc | 600 |
| cgcaacaatt | ttgaaggtga | gatcaccaag | gagaagctat | tagacttcat | caagcacaac | 660 |
| cagctgcctt | tggtcatcga | gttcactgaa | cagacagctc | caaagatttt | cggaggtgaa | 720 |
| atcaagacac | atattctgct | gttcctgccc | aagagtgtgt | ctgactacga | tggcaaattg | 780 |
| agcaacttta | agaaagcggc | cgagggcttt | aagggcaaga | tcctgttcat | cttcatcgat | 840 |
| agtgaccaca | ctgacaacca | gcgcatactt | gagttctttg | gcctgaagaa | ggaggaatgt | 900 |
| ccagctgtgc | ggcttattac | cctttgatgaa | gatatgacca | gtacaaacc | ggagtcgacc | 960 |
| gagctgacag | ctgagaagat | cacacaattt | gccaccact | tcctggaggg | caagatcaag | 1020 |
| cccccacctga | tgagccagga | actgcctgaa | gactgggaca | agcagccagt | gaaagtgcta | 1080 |
| gttgggaaaa | actttgagga | ggttgctttt | gatgagaaaa | agaacgtgtt | tgttgaattc | 1140 |
| tatgctccct | ggtgtggtca | ctgcaagcag | ctagccccga | tttgggataa | actgggagag | 1200 |
| acatacaaag | accatgagaa | tatcgtcatc | gctaagatgg | actcaacagc | caatgaggtg | 1260 |
| gaagctgtga | aggtgcacag | ctttcccaca | ctcaagttct | tcccagcaag | tgcagacaga | 1320 |
| acggtcattg | attacaacgg | tgagcggaca | ctagatggtt | ttaagaaatt | cttggagagc | 1380 |
| ggtggccagg | atggagcggg | ggacaatgac | gacctcgacc | tagaagaagc | tttagagcca | 1440 |
| gatatggaag | aagacgacga | tcagaaagcc | gtgaaggatg | aactg | | 1485 |

<210> SEQ ID NO 42
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: a or g
<220> FEATURE:
<221> NAME/KEY: modified_base
<222> LOCATION: (5)..(5)
<223> OTHER INFORMATION: a or g

```
<220> FEATURE:
<221> NAME/KEY: modified_base
<222> LOCATION: (8)..(8)
<223> OTHER INFORMATION: a or g

<400> SEQUENCE: 42
anganganat g                                                          11

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asp Asp Asp Asp Lys
1               5

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Glu Asn Leu Tyr Phe Gln
1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Lys-beta-naphtylamide

<400> SEQUENCE: 45

Gly Asp Asp Asp Asp Lys
1               5
```